United States Patent
Sun et al.

(10) Patent No.: US 9,283,213 B2
(45) Date of Patent: Mar. 15, 2016

(54) DIHYDROPYRIDIN-2(1H)-ONE COMPOUNDS AS S-NITROSOGLUTATHIONE REDUCTASE INHIBITORS AND NEUROKININ-3 RECEPTOR ANTAGONISTS

(71) Applicant: N30 Pharmaceuticals, Inc., Boulder, CO (US)

(72) Inventors: Xicheng Sun, Broomfield, CO (US); Jian Qiu, Longmont, CO (US)

(73) Assignee: Nivalis Therapeutics, Inc., Boulder, CO (US)

( * ) Notice: Subject to any disclaimer, the term of this patent is extended or adjusted under 35 U.S.C. 154(b) by 0 days.

(21) Appl. No.: 14/598,202

(22) Filed: Jan. 15, 2015

(65) Prior Publication Data
US 2015/0157616 A1 Jun. 11, 2015

Related U.S. Application Data

(62) Division of application No. 13/805,626, filed as application No. PCT/US2011/043374 on Jul. 8, 2011, now Pat. No. 8,946,434.

(60) Provisional application No. 61/365,225, filed on Jul. 16, 2010.

(51) Int. Cl.
| | |
|---|---|
| C07D 401/00 | (2006.01) |
| C07D 419/00 | (2006.01) |
| C07D 213/22 | (2006.01) |
| C07D 417/04 | (2006.01) |
| C07D 417/14 | (2006.01) |
| C07D 417/00 | (2006.01) |
| C07D 405/00 | (2006.01) |
| C07D 403/00 | (2006.01) |
| C07D 409/00 | (2006.01) |
| C07D 411/00 | (2006.01) |
| C07D 413/00 | (2006.01) |
| A61K 31/4412 | (2006.01) |
| C07D 211/88 | (2006.01) |
| C07D 401/04 | (2006.01) |
| C07D 401/14 | (2006.01) |
| C07D 409/14 | (2006.01) |
| C07D 211/86 | (2006.01) |
| C07D 409/04 | (2006.01) |
| A61K 31/4436 | (2006.01) |
| A61K 31/4439 | (2006.01) |
| A61K 31/444 | (2006.01) |

(52) U.S. Cl.
CPC .......... *A61K 31/4412* (2013.01); *A61K 31/444* (2013.01); *A61K 31/4436* (2013.01); *A61K 31/4439* (2013.01); *C07D 211/86* (2013.01); *C07D 211/88* (2013.01); *C07D 401/04* (2013.01); *C07D 401/14* (2013.01); *C07D 409/04* (2013.01); *C07D 409/14* (2013.01)

(58) Field of Classification Search
None
See application file for complete search history.

(56) References Cited

U.S. PATENT DOCUMENTS

| | | | |
|---|---|---|---|
| 3,829,426 A | 8/1974 | Schroder et al. | |
| 4,431,651 A | 2/1984 | Lesher et al. | |
| 4,442,100 A | 4/1984 | Meyer et al. | |
| 5,434,158 A | 7/1995 | Shah | |
| 5,855,654 A | 1/1999 | Willingham et al. | |
| 5,968,923 A | 10/1999 | MacKenzie | |
| 6,262,075 B1 | 7/2001 | MacKenzie | |
| 8,741,915 B2 | 6/2014 | Sun et al. | |
| 8,906,933 B2 | 12/2014 | Sun et al. | |
| 8,946,434 B2 | 2/2015 | Sun et al. | |
| 9,067,893 B2 | 6/2015 | Sun et al. | |
| 2002/0128205 A1 | 9/2002 | Stamler et al. | |
| 2005/0014697 A1 | 1/2005 | Stamler et al. | |
| 2005/0187166 A1 | 8/2005 | Stamler et al. | |
| 2010/0286174 A1 | 11/2010 | Stamler et al. | |
| 2012/0208817 A1 | 8/2012 | Sun et al. | |
| 2013/0096161 A1 | 4/2013 | Sun et al. | |
| 2013/0131093 A1 | 5/2013 | Sun et al. | |
| 2014/0235640 A1 | 8/2014 | Sun et al. | |
| 2015/0224107 A1 | 8/2015 | Sun et al. | |

FOREIGN PATENT DOCUMENTS

| | | |
|---|---|---|
| EP | 0030343 A1 | 6/1981 |
| EP | 2592934 | 8/2015 |
| JP | 10120654 (A) | 5/1998 |
| WO | WO 96/35677 | 11/1996 |
| WO | WO 99/65315 | 12/1999 |
| WO | WO 2004/101742 | 11/2004 |
| WO | WO 2006/034003 | 3/2006 |
| WO | WO 2007/089548 | 8/2007 |
| WO | WO 2007/124494 | 11/2007 |
| WO | WO 2009/076665 | 6/2009 |
| WO | WO 2010/019910 | 2/2010 |

(Continued)

OTHER PUBLICATIONS

Freshney, RI. Culture of Animal Cells: A Manual of Basic Technique. John Wiley and Sons. 2005, 5th Ed., p. 8.*

(Continued)

*Primary Examiner* — Rita Desai
*Assistant Examiner* — Ben S Michelson
(74) *Attorney, Agent, or Firm* — Swanson & Bratschun, L.L.C.

(57) ABSTRACT

The present invention is directed to novel dihydropyridin-2 (1H)-one compounds useful as S-nitrosoglutathione reductase (GSNOR) inhibitors and/or Neurokinin-3 (NK3) receptor antagonists, pharmaceutical compositions comprising such compounds, and methods of making and using the same.

19 Claims, No Drawings

(56) References Cited

FOREIGN PATENT DOCUMENTS

| WO | WO 2010/046780 |  | 4/2010 |
| --- | --- | --- | --- |
| WO | WO 2010/046780 A2 | * | 4/2010 |
| WO | WO 2010/107476 |  | 9/2010 |
| WO | WO 2012/009227 |  | 1/2012 |

OTHER PUBLICATIONS

Dermer, GB. Another Anniversary for the War on Cancer. Bio/Technology. 1994, vol. 12, p. 320.*
Meltzer, H. et al. NK3 receptor antagonists: the next generation of antipsychotics. Nature Reviews. 2005, vol. 4, p. 967.*
Springer, M. et al. Pharmacological inhibition of S-nitrosoglutathione reductase improves endothelial vasodilatory function in rats in vivo. J. Appl. Physiol. 2013, vol. 114, p. 752.*
Akbar et al. (2009) Aliment Pharmaco Ther. 30:423-435, "Review article: visceral hypersensitivity in irritable bowel syndrome: molecular mechanisms and therapeutic agents".
Albert et al. (2006) Neurokinin-3 receptor antagonists in schizophrenia *Exprt Opin. Ther. Patents*, 16(7):925-937.
Blaney et al. (2001) "Stepwise Modulation of Neurokinin-3 and Neurokinin-2 Receptor Affinity and Selectivity in Quinoline Tachykinin Receptor Antagonists", *J. Med. Chem.*, 44(11):1675-1689.
Brooks et al. (1998) Environmental Health Properties 106:1439, "Bioassay-directed Franctionation and Chemical Identification of Mutagens in Bioremediated Soils".
Bueno et al. (2002) Gut 51: i19-i23: doi: 10.1136/gut.51.suppl_1.i19 "Visceral perception: inflammatory and non-inflammatory mediators".
de Belder et al. (May 1994) "Effects of S-nitroso-glutathione in the human forearm circulation; evidence for selective inhibition of platelet activation", *Cardiovasc Res.*, 28(5):691-694.
de Jesus-Berrios et al. (Nov. 2003) "Enzymes that Counteract Nitrosative Stress Promot Fungal Virulence", *Curr. Biol.*, 13:1963-1968.
El-Kholy (1982) Journal of Heterocyclic Chemistry 19(6), 1329-1334, "Preparation and Reactions of 3,4-Dihydro-2*H*-pyran-2-ones".
Essawy et al (Oct. 1978) Indian Journal of Chemistry, Section B: Organic Chemistry Including Medicinal Chemistry 16B(10), 880-883, "Some Reactions of Michael Adducts of α-Phenylchalkone with Ketones, Ethyl Phenylacetate, p-Chlorobenzl Cyanide & Malononitrile".
European Search Report issued Dec. 20, 2013 in European Patent Application Serial No. 11807317.0.
Foster et al. (Apr. 2003) "S-nitrosylation in health and disease", *Trends in Molecular Medicine*, 9(4):160-168.
Foster et al. (2009) "Protein S-nitrosylation in health and disease: a current perspective" Trends in Molecular Medicine,15(9):391-404.
Gaston et al. (Dec. 1993) "Endogenous nitrogen oxides and bronchodilator *S*-nitrosolthiols in human airways", *Proc. Natl. Acad. Sci. USA*, 90:10957-10961.
Harris et al. (2006) "Irritable Bowel Syndrome and Chronic Constipation: Emerging Drugs, Devices and Surgical Treatments" *Current Gastroenterology Reports* 8:282-290.
International Preliminary Report on Patentability for PCT/US2011/043374 mailed Jan. 31, 2013.
International Search Report and Written Opinion issued in PCT/US2011/043374 mailed Dec. 1, 2011.
Jensen et al. (1998) "*S*-Nitrosoglutathione is a substrate for rat alcohol dehydrognease class III isoenzyme", *Biochem J.*, 331:659-668.
Kaposzta et al. (Dec. 2002) "*S*-Nitrosoglutathione Reduces Asymptomatic Embolization After Carotid Angioplasty", *Circulation*, 106(24):3057-3062.
Lipton et al. (Sep. 2001) "*S*-Nitrosothiols signal the ventilatory response to hypoxia", *Nature*, 413:171-174.
Liu et al. (Feb. 2004) "Essential Roles of *S*-Nitrosothiols in Vascular Homeostatsis and Endotoxic Shock", *Cell*, 116(4):617-628.
Liu et al. (Mar. 2001) "A metabolic enzyme for *S*-nitrosothiol conserved from bacterial to humans", *Nature*, 410:490-494.
Maggio (1988)"Tachykinins" *Ann. Rev. Neurosci.* 11:13-28.
Malherbe et al. (2009) "Identification of a Critical Residue in the Transmembrane Domain 2 of Tachykinin Neurokinin 3 Receptor Affecting the Dissociation Kinetics and Antagonism Mode of Osanetant (SR 142801) and Piperidine-Based Structures", *Journal of Medicinal Chemistry* 52:7103-7112.
Meltzer et al. (2006) "NK3 receptor antagonists for the treatment of schizophrenia", *Drug Discovery Today: Therapeutic Strategies*, 3(4):555-560.
Que et al. (Jun. 2005) "Protection from Experimental Asthma by an Endogenous Bronchodilator", *Science*, 308(5728):1618-1621.
Redington, Anthony (2006) "Modulation of Nitric Oxide Pathways: Therapeutic potential in asthma and chronic obstructive pulmonary disease", European Journal of Pharmacology, 533:263-276.
Ricciardolo et al. (2006) "Reactive nitrogen species in the respiratory tract" European Journal of Pharmacology, 533:240-252.
Sanger (2004) "Neurokin NK1 and NK3 receptors as targets for drugs to treat gastrointestinal motility disorders and pain" *British Journal of Pharmacology* 141:1303-1312.
Sanghani et al. (2000) "Kinetic Mechanism of Human Glutathioone-Dependent Formaldehyde Dehydrogenase", *Biochemistry*, 39:10720-10729.
Sanghani et al. (2002) "Human Glutathione-Dependent Formaldehyde Dehydrognease. Structures of Apo, Binary, and Inhibitory Ternary Complexes", *Biochemistry*,41:10778-10786.
Snyder et al. (2002) "Acute Effects of Aerosolized S-Nitrosoglutathione in Cystic Fibrosis", American Journal of Respiratory and Critical Care Medicine, 165:922-926.
Spooren et al. (Dec. 2005) "NK$_3$ receptor antagonists: the next generation of antipsychotics?" Nature Reviews 4:967-975.
Staab et al. (2008) "Dual functions of alcohol dehydrogenase 3: implications with focus on formaldehyde dehydrogenase and S-nitroglutathione reductase activities", *Cell Mol. Life Sci*, 65:3950-3960.
Staab et al. (Jun. 15, 2009) "Medium-chain fatty acids and glutathione derivatives as inhibitors of S-nitrosoglutathione reduction mediated by alcohol dehydrogenase 3", *Chemico-Biological Interactions* 180(1):113-118.
Stamler et al. (Aug. 1992) "Nitric oxide circulates in mammalian plasma primarily as an *S*-nitrose adduct of serium albumin", *Proc. Natl. Acad. Sci. USA*, 89:7674-7677.
Uotila and Koivusalo (1989) Coenzymes and Cofactors vol. 3: Glutathione, part A., D. Dolphin, ed. pp. 517-551 (New York, John Wiley & Sons).
Zaman et al. (2001) "*S*-Nitrosoglutathione Increases Cystic Fibrosis Transmembrane Regulator Maturation", *Biochem Biophys Res Commun.*, 284:65-70.

\* cited by examiner

DIHYDROPYRIDIN-2(1H)-ONE COMPOUNDS AS S-NITROSOGLUTATHIONE REDUCTASE INHIBITORS AND NEUROKININ-3 RECEPTOR ANTAGONISTS

RELATED APPLICATIONS

This application is a divisional of U.S. application Ser. No. 13/805,626, filed Dec. 19, 2012. U.S. application Ser. No. 13/805,626 is a 35 U.S.C. §371 national phase application of International Application Serial No. PCT/US2011/043374, filed Jul. 8, 2011 (WO 2012/009227). International Application Serial No. PCT/US2011/043374 claims priority to U.S. Provisional Application Ser. No. 61/365,225, filed Jul. 16, 2010. Each of these references is incorporated herein by reference in their entirety.

FIELD OF THE INVENTION

The present invention is directed to novel dihydropyridin-2(1H)-one compounds, pharmaceutical compositions comprising such compounds, and methods of making and using the same. These compounds are useful as inhibitors of S-nitrosoglutathione reductase (GSNOR) and/or antagonists of the Neurokinin-3 (NK3) receptor.

BACKGROUND OF THE INVENTION

The chemical compound nitric oxide is a gas with chemical formula NO. NO is one of the few gaseous signaling molecules known in biological systems, and plays an important role in controlling various biological events. For example, the endothelium uses NO to signal surrounding smooth muscle in the walls of arterioles to relax, resulting in vasodilation and increased blood flow to hypoxic tissues. NO is also involved in regulating smooth muscle proliferation, platelet function, neurotransmission, and plays a role in host defense. Although nitric oxide is highly reactive and has a lifetime of a few seconds, it can both diffuse freely across membranes and bind to many molecular targets. These attributes make NO an ideal signaling molecule capable of controlling biological events between adjacent cells and within cells. NO is a free radical gas, which makes it reactive and unstable, thus NO is short lived in vivo, having a half life of 3-5 seconds under physiologic conditions.

In the presence of oxygen, NO can combine with thiols to generate a biologically important class of stable NO adducts called S-nitrosothiols (SNO's). This stable pool of NO has been postulated to act as a source of bioactive NO and as such appears to be critically important in health and disease, given the centrality of NO in cellular homeostasis (Stamler et al., *Proc. Natl. Acad. Sci. USA*, 89:7674-7677 (1992)). Protein SNO's play broad roles in cardiovascular, respiratory, metabolic, gastrointestinal, immune and central nervous system function (Foster et al., 2003, Trends in Molecular Medicine Volume 9, Issue 4, April 2003, pages 160-168). One of the most studied SNO's in biological systems is S-nitrosoglutathione (GSNO) (Gaston et al., *Proc. Natl. Acad. Sci. USA* 90:10957-10961 (1993)), an emerging key regulator in NO signaling since it is an efficient trans-nitrosating agent and appears to maintain an equilibrium with other S-nitrosated proteins (Liu et al., 2001) within cells. Given this pivotal position in the NO—SNO continuum, GSNO provides a therapeutically promising target to consider when NO modulation is pharmacologically warranted.

In light of this understanding of GSNO as a key regulator of NO homeostasis and cellular SNO levels, studies have focused on examining endogenous production of GSNO and SNO proteins, which occurs downstream from the production of the NO radical by the nitric oxide synthetase (NOS) enzymes. More recently there has been an increasing understanding of enzymatic catabolism of GSNO which has an important role in governing available concentrations of GSNO and consequently available NO and SNO's.

Central to this understanding of GSNO catabolism, researchers have recently identified a highly conserved S-nitrosoglutathione reductase (GSNOR) (Jensen et al., *Biochem J.*, 331:659-668 (1998); Liu et al., *Nature*, 410:490-494 (2001)). GSNOR is also known as glutathione-dependent formaldehyde dehydrogenase (GS-FDH), alcohol dehydrogenase 3 (ADH-3) (Uotila and Koivusalo, *Coenzymes and Cofactors.*, D. Dolphin, ed. pp. 517-551 (New York, John Wiley & Sons, 1989)), and alcohol dehydrogenase 5 (ADH-5). Importantly GSNOR shows greater activity toward GSNO than other substrates (Jensen et al., 1998; Liu et al., 2001) and appears to mediate important protein and peptide denitrosating activity in bacteria, plants, and animals. GSNOR appears to be the major GSNO-metabolizing enzyme in eukaryotes (Liu et al., 2001). Thus, GSNO can accumulate in biological compartments where GSNOR activity is low or absent (e.g. airway lining fluid) (Gaston et al., 1993).

Yeast deficient in GSNOR accumulate S-nitrosylated proteins which are not substrates of the enzyme, which is strongly suggestive that GSNO exists in equilibrium with SNO-proteins (Liu et al., 2001). Precise enzymatic control over ambient levels of GSNO and thus SNO-proteins raises the possibility that GSNO/GSNOR may play roles across a host of physiological and pathological functions including protection against nitrosative stress wherein NO is produced in excess of physiologic needs. Indeed, GSNO specifically has been implicated in physiologic processes ranging from the drive to breathe (Lipton et al., *Nature*, 413:171-174 (2001)) to regulation of the cystic fibrosis transmembrane regulator (Zaman et al., *Biochem Biophys Res Commun*, 284: 65-70 (2001), to regulation of vascular tone, thrombosis and platelet function (de Belder et al., Cardiovasc Res. May; 28(5):691-4. (1994); Z. Kaposzta, A et al., Circulation; 106 (24): 3057-3062, 2002) as well as host defense (de Jesus-Berrios et al., *Curr. Biol.*, 13:1963-1968 (2003)). Other studies have found that GSNOR protects yeast cells against nitrosative stress both in vitro (Liu et al., 2001) and in vivo (de Jesus-Berrios et al., 2003).

Collectively data suggest GSNOR as a primary physiological ligand for the enzyme S-nitrosoglutathione reductase (GSNOR), which catabolizes GSNO and consequently reduces available SNO's and NO in biological systems (Liu et al., 2001), (Liu et al., Cell, (2004), 116(4), 617-628), and (Que et al., Science, 2005, 308, (5728):1618-1621). As such, this enzyme plays a central role in regulating local and systemic bioactive NO. Since perturbations in NO bioavailability has been linked to the pathogenesis of numerous disease states, including hypertension, atherosclerosis, thrombosis, asthma, gastrointestinal disorders, inflammation and cancer, agents that regulate GSNOR activity are candidate therapeutic agents for treating diseases associated with nitric oxide imbalance.

Currently, there is a great need in the art for diagnostics, prophylaxis, ameliorations, and treatments for medical conditions relating to increased NO synthesis and/or increased NO bioactivity. In addition, there is a significant need for novel compounds, compositions and methods for preventing, ameliorating, or reversing other NO-associated disorders. The present invention satisfies these needs.

The mammalian tachykinins, also known as neurokinins, are a family of small peptides that share a common carboxyl-terminal sequence of Phe-X-Gly-Leu-Met-NH$_2$ (Maggio et al., *Annual Rev. Neuroscience* 11:13-28 (1998). The main members of the family are substance P (SP), neurokinin A (NKA) and neurokinin B (NKB). As neurotransmitters these peptides exert their biological activity via three distinct neurokinin (NK) receptors termed neurokinin-1 (NK1), neurokinin-2 (NK2) and neurokinin-3 (NK3). SP binds preferentially to NK1, NKA to NK2 and NKB to NK3. The NK3 receptor is characterized by a predominant expression in the central nervous system (CNS) and its involvement in the modulation of the central monoaminergic (noradenaline and dopamine) and amino acid (GABA) neurotransmission. These properties make the NK3 receptor a potential target for CNS diseases such as schizophrenia (Spooren et al., *Nat. Rev. Drug Discov.* 4:967-975 (2005)).

Schizophrenia is a chronic, severe, and disabling brain disorder that affects about 1% of the world's population. Symptoms begin in early adulthood and are followed by a period of interpersonal and social dysfunction. The symptoms of schizophrenia fall into three broad categories: positive symptoms, negative symptoms, and cognitive symptoms. Positive symptoms include hallucinations, delusions, thought disorders and movement disorders. Negative symptoms include depression, anhedonia, blunted affect, diminished speech and cognitive symptoms include memory and attention deficits as well as social withdrawal.

There is no single cause of schizophrenia however, increased dopamine activity in the mesolimbic pathway of the brain is consistently found in schizophrenic individuals. The lack of knowledge about the exact cause and nature of this disease make development of new drugs difficult. Treatment has been focused on antipsychotic medication which primarily works by suppressing dopamine activity. As these drugs have evolved through the years the side effect profile has improved but they still exhibit some side effects such as weight gain. In 2004 Sanofi-Synthelabo published clinical results for Osanetant which was identified as a potent and selective antagonist of the NK3 receptor for the treatment of schizophrenia and in 2005 GSK published clinical results for talnetant which was shown to ameliorate the cognitive issues of schizophrenics however, both compounds have poor pharmacokinetics and pharmacodynamic properties including poor solubility, poor bioavailability, relatively high clearance and poor brain-blood barrier penetration. In spite of the liabilities with these compounds, clinical results to date suggest that the NK3 receptor may prove to be a promising target for treatment of schizophrenia providing that pharmacokinetic and pharmacodynamic issues can be resolved.

Irritable bowel syndrome (IBS) is a chronic, episodic functional gastrointestinal (GI) disorder characterized by abdominal pain/discomfort and altered bowel habit (constipation, diarrhea or alternating periods of both). Patients often experience additional symptoms such as bloating, sensation of incomplete evacuation, straining (constipation) and urgency (diarrhea). IBS patients can experience symptoms for many years, with an average duration of 10 or more years. IBS is often unrecognized or untreated, with as few as 25% of IBS sufferers seeking professional health care. IBS prevalence is estimated to be up to 20% of the population. Functional bowel disorders such as IBS are characterized by visceral hypersensitivity defined by reduced pain and discomfort thresholds, which may manifest as pain associated with bowel disturbances (Akbar et al., *Alimentary Pharmacology and Therapeutics*, 30(5): 423-435 (2009)). Although the pathogenesis of visceral hypersensitivity is not fully understood, several mechanisms have been proposed including subtle inflammation, psychosocial factors and altered sensorimotor function of the gut, a major component of which is believed to be peripheral and central sensitization of visceral afferent neuronal pathways. Similarly, the other functional bowel disorders such as noncardiac chest pain, functional dyspepsia and functional abdominal pain present commonly and treatment of these disorders can be challenging. Over the past 30 years, the main treatment of irritable bowel syndrome has aimed to normalize gastrointestinal transit using either laxatives or antidiarrheal agents, with or without the concurrent use of spasmolytics. These therapeutic options are limited and often disappointing in efficacy.

Recent investigation into the pathophysiology of irritable bowel syndrome has focused on evaluation of visceral hypersensitivity (Bueno et al. *Gut*, 51 (Suppl):19-23 (2002)). At the same time, more information has been acquired on the status of the local immune system as a possible cause for sensitization of nerve terminals. Such investigations have stimulated the emergence of new concepts and original candidate drugs for the treatment of this functional disorder.

Tachykinin receptors do not appear to play significant roles in normal GI functions, but may be involved in defensive or pathological processes. NK3 receptors have been found to mediate certain disruptions of intestinal motility. The activity may be driven by tachykinins released from intrinsic primary afferent neurones (IPANs), which induce slow excitatory postsynaptic potential (EPSP) activity in connecting IPANs and hence, a degree of hypersensitivity within the enteric nervous system. The same process is also proposed to increase C-fibre sensitivity, either indirectly or directly. Thus, NK3 receptor antagonists inhibit intestinal nociception via a "peripheral" mechanism that may be intestine-specific. Studies with talnetant and other selective NK3 receptor antagonists revealed an exciting and novel pathway by which pathological changes in intestinal motility and nociception can be induced, suggesting a role for NK3 receptor antagonism in irritable bowel syndrome (Sanger, *Brit. J. of Pharm.*, 141: 1303-1312 (2004)).

Currently, there is a great need in the art for diagnostics, prophylaxis, ameliorations, and treatments for medical conditions relating to a disease or condition characterized by overstimulation of NK3. In addition, there is a significant need for novel compounds, compositions and methods for preventing, ameliorating, or reversing other NK3 associated disorders. The present invention satisfies these needs.

SUMMARY OF THE INVENTION

The present invention provides novel dihydropyridin-2 (1H)-one compounds. These compounds are useful as S-nitrosoglutathione reductase ("GSNOR") inhibitors and/or Neurokinin-3 ("NK3") receptor antagonists. The invention encompasses pharmaceutically acceptable salts, prodrugs, and metabolites of the described compounds. Also encompassed by the invention are pharmaceutical compositions comprising at least one compound of the invention and at least one pharmaceutically acceptable carrier.

The compositions of the present invention can be prepared in any suitable pharmaceutically acceptable dosage form.

The present invention provides a method for inhibiting S-nitrosoglutathione reductase in a subject in need thereof. Such a method comprises administering a therapeutically effective amount of a pharmaceutical composition comprising at least one GSNOR inhibitor or a pharmaceutically acceptable salt thereof, a prodrug or metabolite thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a disorder ameliorated by NO donor therapy in a subject in need thereof. Such a method comprises administering a therapeutically effective amount of a pharmaceutical composition comprising at least one GSNOR inhibitor or a pharmaceutically acceptable salt thereof, a prodrug, or metabolite thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a cell proliferative disorder in a subject in need thereof. Such a method comprises administering a therapeutically effective amount of a pharmaceutical composition comprising at least one GSNOR inhibitor or a pharmaceutically acceptable salt thereof, a prodrug, or metabolite thereof, in combination with at least one pharmaceutically acceptable carrier. The GSNOR inhibitor can be a novel compound according to the invention, or it can be a known compound which previously was not known to be an inhibitor of GSNOR.

The methods of the invention encompass administration with one or more secondary active agents. Such administration can be sequential or in a combination composition.

The present invention also provides novel dihydropyridin-2(1H)-one compounds useful as neurokinin-3 receptor antagonists. The tachykinins, substance P (SP), neurokinin A (NKA), and neurokinin B (NKB), are structurally similar members of a family of neuropeptides. Each of these is an agonist of the receptor types, neurokinin-1 receptor (NK1), neurokinin-2 receptor (NK2), and neurokinin-3 receptor (NK3), which are so defined according to their unique amino acid sequence and their relative abilities to bind tachykinins with high affinity and to be activated by the natural agonists, SP, NKA, and NKB, respectively (see also U.S. Pat. No. 5,434,158, which is herein incorporated by reference). In some embodiments, the dihydropyridin-2(1H)-ones of the present invention are NK3 receptor antagonists.

The present invention provides a method for antagonizing the neurokinin-3 (NK3) receptor. Such a method comprises administering a therapeutically effective amount of a pharmaceutical composition comprising at least one NK3 receptor antagonist or a pharmaceutically acceptable salt thereof, a prodrug or metabolite thereof, in combination with at least one pharmaceutically acceptable carrier. The NK3 receptor antagonist can be a novel compound according to the invention, or it can be a known compound which previously was not known to be an NK3 receptor antagonist.

Although methods and materials similar or equivalent to those described herein can be used in the practice or testing of the present invention, suitable methods and materials are described below. All publicly available publications, patent applications, patents, and other references mentioned herein are incorporated by reference in their entirety. In the case of conflict, the present specification, including definitions, will control.

Both the foregoing summary and the following detailed description are exemplary and explanatory and are intended to provide further details of the compositions and methods as claimed. Other objects, advantages, and novel features will be readily apparent to those skilled in the art from the following detailed description.

DETAILED DESCRIPTION OF THE PREFERRED EMBODIMENTS

A. Overview of the Invention

Until recently, S-nitrosoglutathione reductase (GSNOR) was known to oxidize the formaldehyde glutathione adduct, S-hydroxymethylglutathione. GSNOR has since been identified in a variety of bacteria, yeasts, plants and animals and is well conserved. The proteins from *E. coli*, *S. cerevisiae* and mouse macrophages share over 60% amino acid sequence identity. GSNOR activity (i.e., decomposition of S-nitrosoglutathione when NADH is present as a required cofactor) has been detected in *E. coli*, in mouse macrophages, in mouse endothelial cells, in mouse smooth muscle cells, in yeasts, and in human HeLa, epithelial and monocyte cells. Human GSNOR nucleotide and amino acid sequence information can be obtained from the National Center for Biotechnology Information (NCBI) databases under Accession Nos. M29872, NM_000671. Mouse GSNOR nucleotide and amino acid sequence information can be obtained from NCBI databases under Accession Nos. NM_007410. In the nucleotide sequence, the start site and stop site are underlined. CDS designates coding sequence. SNP designates single nucleotide polymorphism. Other related GSNOR nucleotide and amino acid sequences, including those of other species, can be found in U.S. Patent Application 2005/0014697.

In accord with the present invention, GSNOR has been shown to function in vivo and in vitro to metabolize S-nitrosoglutathione (GSNO) and protein S-nitrosothiols (SNOs) to modulate NO bioactivity, by controlling the intracellular levels of low mass NO donor compounds and preventing protein nitrosylation from reaching toxic levels.

Based on this, it follows that inhibition of this enzyme potentiates bioactivity in all diseases in which NO donor therapy is indicated, inhibits the proliferation of pathologically proliferating cells, and increases NO bioactivity in diseases where this is beneficial.

The present invention provides pharmaceutical agents that are potent inhibitors of GSNOR and/or antagonists of the NK3 receptor. In particular, provided are substituted dihydropyridin-2(1H)-one analogs having the structures depicted below (Formula I), or a pharmaceutically acceptable salt, stereoisomer, or prodrug thereof.

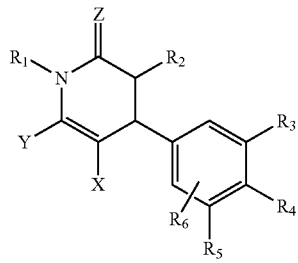

I wherein

X is selected from the group consisting of aryl, substituted aryl, heteroaryl, substituted heteroaryl, cycloalkyl, substituted cycloalkyl, heterocyclyl, and substituted heterocyclyl, each having 6 members or less in the ring;

Y is selected from the group consisting of aryl, substituted aryl, heteroaryl, substituted heteroaryl, cycloalkyl, substituted cycloalkyl, heterocyclyl, and substituted heterocyclyl;

Z is selected from the group consisting of O, S, and $NR_7$;

$R_1$, $R_2$ and $R_7$ are independently selected from the group consisting of hydrogen, and $C_1$-$C_6$ alkyl;

$R_3$ is selected from the group consisting of hydrogen, nitro, cyano, carboxyl, carbamoyl, methylsulfonamido, fluoro, chloro, bromo, hydroxy, methylsulfonyl, and methylsulfinyl, isoxazol-4-yl, $C_1$-$C_6$ alkoxy, —C(NH)NHOH, sulfonic acid, and acetyl;

$R_4$ is selected from the group consisting of hydrogen, hydroxy, methoxy, carboxyl, and tetrazol-5-yl;

wherein, when $R_3$ is hydrogen, then $R_4$ is not hydrogen;

or optionally $R_3$ and $R_4$, taken together can form a heterocycle;

$R_5$ is selected from the group consisting of hydrogen, hydroxyl, carboxy, chloro, fluoro, cyano, —O(CH$_2$)$_{1-6}$NMe$_2$, $C_1$-$C_6$ alkyl, —O(CH$_2$)$_{1-6}$OCH$_3$, —O(CH$_2$)$_{1-6}$OH, acetyl, CF$_3$, and $C_1$-$C_6$ alkoxy;

or optionally $R_4$ and $R_5$, taken together can form a heterocycle; and $R_6$ is selected from the group consisting of hydrogen and hydroxyl.

As used in this context, the term "analog" refers to a compound having similar chemical structure and function as compounds of Formula I that retains the dihydropyridin-2(1H)-one ring.

Some dihydropyridin-2(1H)-one analogs of the invention can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of a compound including tautomeric forms of the compound.

Illustrative compounds having asymmetric centers can exist in different enantiomeric and diastereomeric forms. A compound can exist in the form of an optical isomer or a diastereomer. Accordingly, the invention encompasses compounds in the forms of their optical isomers, diastereomers and mixtures thereof, including racemic mixtures.

It should be noted that if there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of the described compound.

B. S-Nitrosoglutathione Reductase Inhibitors and/or NK3 Receptor Antagonists

1. Inventive Compounds

In one of its aspects the present invention provides a compound having a structure shown in Formula I, or a pharmaceutically acceptable salt, stereoisomer, or prodrug thereof:

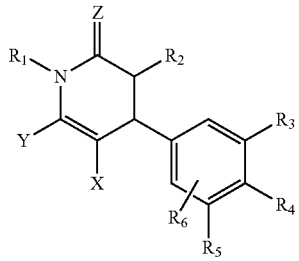

wherein

X is selected from the group consisting of aryl, substituted aryl, heteroaryl, substituted heteroaryl, cycloalkyl, substituted cycloalkyl, heterocyclyl, and substituted heterocyclyl, each having 6 members or less in the ring;

Y is selected from the group consisting of aryl, substituted aryl, heteroaryl, substituted heteroaryl, cycloalkyl, substituted cycloalkyl, heterocyclyl, and substituted heterocyclyl;

Z is selected from the group consisting of O, S, and $NR_7$;

$R_1$, $R_2$ and $R_7$ are independently selected from the group consisting of hydrogen, and $C_1$-$C_6$ alkyl;

$R_3$ is selected from the group consisting of hydrogen, nitro, cyano, carboxyl, carbamoyl, methylsulfonamido, fluoro, chloro, bromo, hydroxyl, methylsulfonyl, and methylsulfinyl, isoxazol-4-yl, $C_1$-$C_6$ alkoxy, —C(NH)NHOH, sulfonic acid, and acetyl;

$R_4$ is selected from the group consisting of hydrogen, hydroxyl, methoxy, carboxyl, and tetrazol-5-yl;

wherein, when $R_3$, is hydrogen, then $R_4$ is not hydrogen;

or optionally $R_3$ and $R_4$, taken together can form a heterocycle; and $R_5$ is selected from the group consisting of hydrogen, hydroxyl, carboxyl, chloro, fluoro, cyano, —O (CH$_2$)$_{1-6}$NMe$_2$, $C_1$-$C_6$ alkyl, —O(CH$_2$)$_{1-6}$OCH$_3$, —O (CH$_2$)$_{1-6}$OH, acetyl, CF$_3$, and $C_1$-$C_6$ alkoxy;

or optionally $R_4$ and $R_5$, taken together can form a heterocycle; and $R_6$ is selected from the group consisting of hydrogen and hydroxyl.

In a further aspect of the invention, R4 is selected from the group consisting of hydroxyl, carboxyl, and tetrazol-5-yl.

In a further aspect of the invention, R1, R2 and R7 are independently selected from the group consisting of hydrogen and methyl;

$R_3$ is selected from the group consisting of hydrogen, nitro, cyano, carboxyl, carbamoyl, methylsulfonamido, fluoro, chloro, bromo, hydroxyl, methylsulfonyl, and methylsulfinyl, isoxazol-4-yl, $C_1$-$C_6$ alkoxy, —C(NH)NHOH, sulfonic acid, acetyl;

$R_4$ is selected from the group consisting of hydroxyl, carboxyl, and tetrazol-5-yl;

$R_5$ is selected from the group consisting of hydrogen, hydroxyl, carboxy, chloro, fluoro, cyano, —O(CH$_2$)$_2$NMe$_2$, $C_1$-$C_6$ alkyl, —O(CH$_2$)$_2$OCH$_3$, —O(CH$_2$)$_2$OH, acetyl, CF$_3$, methoxy, ethoxy, isopropoxy, and n-propoxy; and $R_6$ is hydrogen.

In a further aspect of the invention, $R_3$ is selected from the group consisting of hydrogen, nitro, and hydroxyl; $R_4$ is selected from the group consisting of hydroxyl, carboxyl, and tetrazol-5-yl; and $R_5$ is selected from the group consisting of hydrogen, ethoxy, fluoro, and —O(CH$_2$)$_2$OH.

In a further aspect of the invention, suitable identities for X include, but are not limited to aryl, substituted aryl, heteroaryl, and substituted heteroaryl.

In a further aspect of the invention, suitable identities for X include, but are not limited to phenyl, substituted phenyl, thiophen-yl, substituted thiophen-yl, thiazol-yl, substituted thiazol-yl, pyrazin-yl, substituted pyrazin-yl, pyridin-yl, and substituted pyridin-yl, cyclohexyl, substituted cyclohexyl.

In a further aspect of the invention, suitable identities for X include, but are not limited to, phenyl, thiophen-2-yl, thiophen-3-yl, thiazol-2-yl, 2-fluorophenyl, p-tolyl, m-tolyl, biphenyl-4-yl, 4-methoxyphenyl, 3-chlorophenyl, 3,4-dichlorophenyl, 3-methoxyphenyl, 3,4-dimethoxyphenyl, 4-bromophenyl, o-tolyl, 4-chlorophenyl, 2-chlorophenyl, 3-cyanophenyl, 3,4-difluorophenyl, 4-cyanophenyl, 3-carbamoylphenyl, pyrazin-2-yl, biphenyl-3-yl, 2-cyanophenyl, pyridin-4-yl, and pyridin-3-yl, 4-(dimethylamino)phenyl, 3-fluorophenyl, 3-ethylphenyl, and cyclohexyl.

In a further aspect of the invention, suitable identities for X include, but are not limited to, phenyl, thiophen-2-yl, thiophen-3-yl, and pyridin-3-yl.

In a further aspect of the invention, suitable identities for Y include, but are not limited to aryl, substituted aryl, heteroaryl, substituted aryl, cycloalkyl, and substituted cycloalkyl.

In a further aspect of the invention, suitable identities for Y include, but are not limited to phenyl, substituted phenyl, thiophen-yl, substituted thiophen-yl, thiazol-yl, substituted thiazol-yl, pyrazin-yl, substituted pyrazin-yl, pyridin-yl, substituted pyridin-yl, furan-yl, substituted furan-yl, benzo[d][1,3]dioxol-yl, substituted benzo[d][1,3]dioxol-yl, imidazol-yl, substituted imidazol-yl, naphthalen-yl, substituted naphthalen-yl, pyrrol-yl, substituted pyrrol-yl, pyrazol-yl, substituted pyrazol-yl, tetrahydrofuran-yl, substituted tetrahydrofuran-yl, cyclopentyl, substituted cyclopentyl, cyclohexyl, and substituted cyclohexyl.

In a further aspect of the invention, suitable identities for Y include, but are not limited to, phenyl, 3-methoxyphenyl, p-tolyl, 4-methoxyphenyl, 3,5-dichlorophenyl, 3-fluorophenyl, 4-bromophenyl, biphenyl-4-yl, 4-fluorophenyl, 4-chlorophenyl, 3-chlorophenyl, 3,4-dimethoxyphenyl, 3-fluoro-4-methoxyphenyl, 4-chloro-3-fluorophenyl, 3-chloro-4-fluorophenyl, 3,4-difluorophenyl, 3,5-difluorophenyl, 3,4-dichlorophenyl, 4-hydroxyphenyl, 2,4-difluorophenyl, furan-3-yl, 2-chlorophenyl, 3-cyanophenyl, 4-(dimethylamino)phenyl, 2-fluorophenyl, 4-morpholinophenyl, 4-aminophenyl, pyridin-2-yl, benzo[d][1,3]dioxol-5-yl, 4-cyanophenyl, pyridin-3-yl, pyridin-4-yl, 4-acetamidophenyl, thiophen-2-yl, thiophen-3-yl, 1-methyl-1H-imidazol-4-yl, naphthalen-1-yl, methyl phenylcarbamate, and naphthalen-2-yl, 4-(methanesulfonamido)phenyl, 1H-pyrrol-3-yl, 1-(phenylsulfonyl)-1H-pyrrol-3-yl, furan-2-yl, 4-(trifluoromethyl)phenyl, o-tolyl, 1-methyl-1H-pyrazol-4-yl, 1-methyl-1H-pyrazol-3-yl, 3-chloro-5-fluorophenyl, 3-hydroxyphenyl, pyrazin-2-yl, quinolin-6-yl, isoquinolin-6-yl, 1-methyl-1H-pyrazol-5-yl, tetrahydrofuran-2-yl, cyclopentyl, tetrahydrofuran-3-yl, and cyclohexyl.

In a further aspect of the invention, suitable identities for Y include, but are not limited to phenyl, pyridin-3-yl, 1-methyl-1H-pyrazol-4-yl, and cyclohexyl.

In a further aspect of the invention, Z is O.

In a further aspect of the invention, suitable compounds of formula I include, but are not limited to:
4-(3-ethoxy-4-hydroxy-5-nitrophenyl)-5,6-diphenyl-3,4-dihydropyridin-2(1H)-one;
4-(3-ethoxy-4-hydroxy-5-nitrophenyl)-6-(pyridin-3-yl)-5-(thiophen-3-yl)-3,4-dihydropyridin-2(1H)-one;
4-(4-(2H-tetrazol-5-yl)phenyl)-5-phenyl-6-(pyridin-3-yl)-3,4-dihydropyridin-2(1H)-one;
4-(3-ethoxy-4-hydroxy-5-nitrophenyl)-6-(1-methyl-1H-pyrazol-4-yl)-5-(thiophen-3-yl)-3,4-dihydropyridin-2(1H)-one;
4-(4-(2H-tetrazol-5-yl)phenyl)-6-(1-methyl-1H-pyrazol-4-yl)-5-(thiophen-3-yl)-3,4-dihydropyridin-2(1H)-one;
2-hydroxy-4-(2-oxo-5,6-diphenyl-1,2,3,4-tetrahydropyridin-4-yl)benzoic acid;
2-hydroxy-4-(2-oxo-6-phenyl-5-(thiophen-3-yl)-1,2,3,4-tetrahydropyridin-4-yl)benzoic acid;
4-(4-(2H-tetrazol-5-yl)phenyl)-6-(1-methyl-1H-pyrazol-4-yl)-5-phenyl-3,4-dihydropyridin-2(1H)-one;
2-hydroxy-4-(6-(1-methyl-1H-pyrazol-4-yl)-2-oxo-5-(thiophen-3-yl)-1,2,3,4-tetrahydropyridin-4-yl)benzoic acid;
2-fluoro-6-hydroxy-4-(2-oxo-5,6-diphenyl-1,2,3,4-tetrahydropyridin-4-yl)benzoic acid;
2-fluoro-6-hydroxy-4-(6-(1-methyl-1H-pyrazol-4-yl)-2-oxo-5-(thiophen-3-yl)-1,2,3,4-tetrahydropyridin-4-yl)benzoic acid;
2-ethoxy-6-hydroxy-4-(2-oxo-5,6-diphenyl-1,2,3,4-tetrahydropyridin-4-yl)benzoic acid;
4-(6-cyclohexyl-2-oxo-5-(thiophen-3-yl)-1,2,3,4-tetrahydropyridin-4-yl)-2-fluoro-6-hydroxybenzoic acid;
4-(4-hydroxy-3-(2-hydroxyethoxy)-5-nitrophenyl)-5,6-diphenyl-3,4-dihydropyridin-2(1H)-one;
2-fluoro-6-hydroxy-4-(1-methyl-2-oxo-5,6-diphenyl-1,2,3,4-tetrahydropyridin-4-yl)benzoic acid;
4-(3-ethoxy-4-hydroxy-5-nitrophenyl)-1-methyl-5,6-diphenyl-3,4-dihydropyridin-2(1H)-one;
and
2-fluoro-6-hydroxy-4-(6-(1-methyl-1H-pyrazol-4-yl)-2-oxo-5-(thiophen-2-yl)-1,2,3,4-tetrahydropyridin-4-yl)benzoic acid.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

It is to be understood that isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

2. Representative Compounds

Examples 1-17 list representative novel dihydropyridin-2 (1H)-one analogs of Formula I. The synthetic methods that can be used to prepare each compound are detailed in Examples 1-17, with reference to intermediates described in Example 18. Supporting mass spectrometry data and proton NMR data for each compound is also included in Examples 1-17.

GSNOR inhibitor activity was determined by the assay described in Example 19 and $IC_{50}$ values were obtained. GSNOR inhibitor compounds in Examples 1-17 had an $IC_{50}$ of about <1.0 µM. GSNOR inhibitor compounds in Examples 1-2, 4, 6-7, 9-14, and 17 had an $IC_{50}$ of about <0.1 µM.

NK3 receptor antagonist activity was determined for a subset of the 17 compounds. A percent inhibition value at the concentration of 10 µM was determined for selected compounds in the human NK3 receptor binding assay described in Example 20. Compounds in the following Examples had about equal to or greater than 50% inhibition at 10 µM: Examples 1-2, and 4. A percent inhibition value at the concentration of 1 µM was determined for selected compounds in the human NK3 receptor binding assay described in Example 21. The following compounds had about equal to or greater than 50% inhibition at 1 µM: Examples 14 and 16. The human NK3 receptor binding assay described in Example 22 is used to determine $IC_{50}$ values. An $IC_{50}$ of about 1.1 µM was obtained for the compound in Example 1.

In certain embodiments of the invention it has been demonstrated that racemic mixtures have GSNOR inhibitor activity. Without being bound by theory, it is believed that when the enantiomers are separated, one of the enantiomers has the majority of the GSNOR inhibitor activity and the other enantiomer is significantly less active as a GSNOR inhibitor. Without being bound by theory, it is believed that when the enantiomers of a GSNOR inhibitor are separated, the enantiomer which demonstrates significantly better GSNOR inhibitor activity is of the S configuration. It has been shown that a structurally related compound 4-(3-ethoxy-4-hydroxy-5-nitrophenyl)-5,6-diphenyl-3,4-dihydropyrimidin-2(1H)-one has an S configuration by X-ray crystallography when the active enantiomer for GSNOR was crystallized with GSNOR (see PCT application US2010/050164 and PCT application US2010/050186 incorporated herein by reference in their entirety). The S configuration of that compound has an $IC_{50}$ of 11 nM as a GSNOR inhibitor, and an $IC_{50}$ of 19000 nM as an NK3 receptor antagonist. The other enantiomer, the R configuration, has an $IC_{50}$ of 19720 nM as a GSNOR inhibitor, and an $IC_{50}$ of 110 nM as an NK3 receptor antagonist.

In certain embodiments of the invention it has been demonstrated that racemic mixtures have NK3 receptor antagonist activity as well as GSNOR activity. Without being bound by theory, it is believed that when the enantiomers are separated, one of the enantiomers has the majority of the NK3 receptor antagonist activity and the other enantiomer is significantly less active as a NK3 receptor antagonist. Without being bound by theory, it is believed that the enantiomer having substantially reduced GSNOR inhibitor activity has significant activity for the neurokinin receptor NK3 and that the enantiomer which demonstrates significantly better NK3 receptor antagonist activity is of the R configuration.

C. Definitions

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The term "acyl" includes compounds and moieties that contain the acetyl radical ($CH_3CO—$) or a carbonyl group to which a straight or branched chain lower alkyl residue is attached.

The term "alkyl" as used herein refers to a straight or branched chain, saturated hydrocarbon having the indicated number of carbon atoms. For example, ($C_1$-$C_6$) alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein.

The term "alkenyl" as used herein refers to a straight or branched chain unsaturated hydrocarbon having the indicated number of carbon atoms and at least one double bond. Examples of a ($C_2$-$C_8$) alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein.

The term "alkynyl" as used herein refers to a straight or branched chain unsaturated hydrocarbon having the indicated number of carbon atoms and at least one triple bond. Examples of a ($C_2$-$C_8$) alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein.

The term "alkoxy" as used herein refers to an —O-alkyl group having the indicated number of carbon atoms. For example, a ($C_1$-$C_6$) alkoxy group includes —O-methyl, —O-ethyl, —O-propyl, —O-isopropyl, —O-butyl, —O-sec-butyl, —O-tert-butyl, —O-pentyl, —O— isopentyl, —O-neopentyl, —O-hexyl, —O-isohexyl, and —O-neohexyl.

The term "aminoalkyl" as used herein, refers to an alkyl group (typically one to six carbon atoms) wherein one or more of the $C_1$-$C_6$ alkyl group's hydrogen atoms is replaced with an amine of formula —N($R^c$)$_2$, wherein each occurrence of $R^c$ is independently —H or ($C_1$-$C_6$) alkyl. Examples of aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2CH_2N(CH_3)_2$, t-butylaminomethyl, isopropylaminomethyl and the like.

The term "aryl" as used herein refers to a 5- to 14-membered monocyclic, bicyclic or tricyclic aromatic ring system. Examples of an aryl group include phenyl and naphthyl. An aryl group can be unsubstituted or optionally substituted with one or more substituents as described herein below. Examples of aryl groups include phenyl or aryl heterocycles such as, pyrrole, furan, thiophene, thiazole, isothiazole, imidazole, triazole, tetrazole, pyrazole, oxazole, isoxazole, pyridine, pyrazine, pyridazine, and pyrimidine, and the like.

As used herein, the term "bioactivity" indicates an effect on one or more cellular or extracellular process (e.g., via binding, signaling, etc.) which can impact physiological or pathophysiological processes.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxy" or "carboxyl" means a —COOH group or carboxylic acid.

The term "$C_m$-$C_n$" means "m" number of carbon atoms to "n" number of carbon atoms. For example, the term "$C_1$-$C_6$" means one to six carbon atoms ($C_1$, $C_2$, $C_3$, $C_4$, $C_5$ or $C_6$). The term "$C_2$-$C_6$" includes two to six carbon atoms ($C_2$, $C_3$, $C_4$, $C_5$ or $C_6$). The term "$C_3$-$C_6$" includes three to six carbon atoms ($C_3$, $C_4$, $C_5$ or $C_6$).

The term "cycloalkyl" as used herein refers to a 3- to 14-membered saturated or unsaturated non-aromatic monocyclic, bicyclic or tricyclic hydrocarbon ring system. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, and tetrahydroheptalene, (1s,3s)-bicyclo[1.1.0]butane, bicyclo[1.1.1]pentane, bicyclo[2.1.1]hexane, Bicyclo[2.2.1]heptane, bicyclo[2.2.2]octane, bicyclo[3.1.1]heptane, bicyclo[3.2.1]octane, bicyclo[3.3.1]nonane, bicyclo[3.3.2]decane, bicyclo[3.3.]undecane, bicyclo[4.2.2]decane, bicyclo[4.3.1]decane. A cycloalkyl group can be unsubstituted or optionally substituted with one or more substituents as described herein below.

The term "halogen" includes fluorine, bromine, chlorine, iodine, etc.

The term "haloalkyl," as used herein, refers to a $C_1$-$C_6$ alkyl group wherein from one or more of the $C_1$-$C_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroalkyl," by itself or in combination with another term, means, unless otherwise stated, a stable straight or branched chain alkyl, or combinations thereof, consisting of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S can be placed at any position of the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, and —$CH_2$—CH=N—$OCH_3$. Up to two heteroatoms can be consecutive, such as, for example, —$CH_2$—NH—$OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$.

To further illustrate the definition of a heteroalkyl group, where the heteroatom is oxygen, a heteroalkyl group can be an oxyalkyl group. For instance, ($C_2$-$C_5$) oxyalkyl is meant to include, for example —$CH_2$—O—$CH_3$ (a $C_3$-oxyalkyl group with two carbon atoms and one oxygen replacing a carbon atom), —$CH_2CH_2CH_2CH_2OH$, —$OCH_2CH_2OCH_2CH_2OH$, —$OCH_2CH(OH)CH_2OH$, and the like.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thienyl, benzothienyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl and oxazolyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" refers to 3- to 14-membered ring systems which are either saturated, unsaturated, or aromatic, and which contains from 1 to 4 heteroatoms independently selected from nitrogen, oxygen and sulfur, and wherein the nitrogen and sulfur heteroatoms can be optionally oxidized, and the nitrogen heteroatom can be optionally quaternized, including, including monocyclic, bicyclic, and tricyclic ring systems. The bicyclic and tricyclic ring systems may encompass a heterocycle or heteroaryl fused to a benzene ring. The heterocycle can be attached via any heteroatom or carbon atom, where chemically acceptable. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thienyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents as described herein below.

The term "heterocycloalkyl," by itself or in combination with other terms, represents, unless otherwise stated, cyclic versions of "heteroalkyl." Additionally, a heteroatom can occupy the position at which the heterocycle is attached to the remainder of the molecule. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "hydroxyalkyl," as used herein, refers to an alkyl group having the indicated number of carbon atoms wherein one or more of the hydrogen atoms in the alkyl group is replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH_2CH_2CH_2CH_2CH_2OH$, and branched versions thereof.

The term "hydroxy" or "hydroxyl" includes groups with an —OH or —O$^-$.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. In some embodiments, a stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

As used herein, "protein" is used synonymously with "peptide," "polypeptide," or "peptide fragment". A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, "modulate" is meant to refer to an increase or decrease in the levels of a peptide or a polypeptide, or to increase or decrease the stability or activity of a peptide or a polypeptide. The term "inhibit" is meant to refer to a decrease in the levels of a peptide or a polypeptide or to decrease in the stability or activity of a peptide or a polypeptide. In preferred embodiments, the peptide which is modulated or inhibited is S-nitrosoglutathione (GSNO) or protein S-nitrosothiols (SNOs).

As used here, the terms "nitric oxide" and "NO" encompass uncharged nitric oxide and charged nitric oxide species, particularly including nitrosonium ion ($NO^+$) and nitroxyl ion ($NO^-$). The reactive form of nitric oxide can be provided by gaseous nitric oxide. Compounds having the structure $X-NO_y$, wherein X is a nitric oxide releasing, delivering or transferring moiety, including any and all such compounds which provide nitric oxide to its intended site of action in a form active for their intended purpose, and Y is 1 or 2.

As utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

A "pharmaceutically acceptable salt" or "salt" of a compound of the invention is a product of the disclosed compound that contains an ionic bond, and is typically produced by reacting the disclosed compound with either an acid or a base, suitable for administering to a subject. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

A "pharmaceutical composition" is a formulation comprising the disclosed compounds in a form suitable for administration to a subject. A pharmaceutical composition of the invention is preferably formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

Substituents for the groups referred to as alkyl, heteroalkyl, alkylene, alkenyl, alkynyl, cycloalkyl, heterocycloalkyl, cycloalkenyl and heterocycloalkenyl can be selected from a variety of groups including $-OR^{d\prime}$, =O, $=NR^{d\prime}$, $=N-OR^{d\prime}$, $-NR^{d\prime}R^{d\prime\prime\prime}$, $-SR^{d\prime}$, -halo, $-SiR^{d\prime}R^{d\prime\prime}R^{d\prime\prime\prime}$, $-OC(O)R^{d\prime}$, $-C(O)R^{d\prime}$, $-CO_2R^{d\prime}$, $-CONR^{d\prime}R^{d\prime\prime}$, $-OC(O)NR^{d\prime}R^{d\prime\prime}$, $-NR^{d\prime\prime}C(O)R^{d\prime}$, $-NR^{d\prime\prime}C(O)NR^{d\prime}R^{d\prime\prime}$, $-NR^{d\prime\prime\prime}SO_2NR^{d\prime}R^{d\prime\prime}$, $-NR^{d\prime\prime}CO_2R^{d\prime}$, $-NHC(NH_2)=NH$, $-NR^{a\prime}C(NH_2)=NH$, $-NHC(NH_2)=NR^{d\prime}$, $-S(O)R^{d\prime}$, $-SO_2R^{d\prime}$, $-SO_2NR^{d\prime}R^{d\prime\prime}$, $-NR^{d\prime\prime}SO_2R^{d\prime}$, $-CN$ and $-NO_2$, in a number ranging from zero to three, with those groups having zero, one or two substituents being exemplary. $R^{d\prime}$, $R^{d\prime\prime}$ and $R^{d\prime\prime\prime}$ each independently refer to hydrogen, unsubstituted $(C_1-C_8)$alkyl, unsubstituted hetero$(C_1-C_8)$alkyl, unsubstituted aryl and aryl substituted with one to three substituents selected from -halo, unsubstituted alkyl, unsubstituted alkoxy, unsubstituted thioalkoxy and unsubstituted aryl $(C_1-C_4)$alkyl. When $R^{d\prime}$ and $R^{d\prime\prime}$ are attached to the same nitrogen atom, they can be combined with the nitrogen atom to form a 5-, 6- or 7-membered ring. For example, $-NR^{d\prime}R^{d\prime\prime}$ can represent 1-pyrrolidinyl or 4-morpholinyl.

Typically, an alkyl or heteroalkyl group will have from zero to three substituents, with those groups having two or fewer substituents being exemplary of the present invention. An alkyl or heteroalkyl radical can be unsubstituted or monosubstituted. In some embodiments, an alkyl or heteroalkyl radical will be unsubstituted.

Exemplary substituents for the alkyl and heteroalkyl radicals include but are not limited to $-OR^{d\prime}$, =O, $=NR^{d\prime}$, $=N-OR^{d\prime}$, $-NR^{d\prime}R^{d\prime\prime}$, $-SR^{d\prime}$, -halo, $-SiR^{d\prime}R^{d\prime\prime}R^{d\prime\prime\prime}$, $-OC(O)R^{d\prime}$, $-C(O)R^{d\prime}$, $-CO_2R^{d\prime}$, $-CONR^{d\prime}R^{d\prime\prime}$, $-OC(O)NR^{d\prime}R^{d\prime\prime}$, $-NR^{d\prime\prime}C(O)R^{d\prime}$, $-NR^{d\prime\prime}C(O)NR^{d\prime}R^{d\prime\prime}$, $-NR^{d\prime\prime\prime}SO_2NR^{d\prime}R^{d\prime\prime}$, $-NR^{d\prime\prime}CO_2R^{d\prime}$, $-NHC(NH_2)=NH$, $-NR^{a\prime}C(NH_2)=NH$, $-NHC(NH_2)=NR^{d\prime}$, $-S(O)R^{d\prime}$, $-SO_2R^{d\prime}$, $-SO_2NR^{d\prime}R^{d\prime\prime}$, $-NR^{d\prime\prime}SO_2R^{d\prime}$, $-CN$ and $-NO_2$, where $R^{d\prime}$, $R^{d\prime\prime}$ and $R^{d\prime\prime\prime}$ are as defined above. Typical substituents can be selected from: $-OR^d$, =O, $-NR^{d\prime}R^{d\prime\prime}$, -halo, $-OC(O)R^{d\prime}$, $-CO_2R^{d\prime}$, $-C(O)NR^{d\prime}R^{d\prime\prime}$, $-OC(O)NR^{d\prime}R^{d\prime\prime}$, $-NR^{d\prime\prime}C(O)R^{d\prime}$, $-NR^{d\prime\prime}CO_2R^{d\prime}$, $-NR^{d\prime\prime\prime}SO_2NR^{d\prime}R^{d\prime\prime}$, $-SO_2R^{d\prime}$, $-SO_2NR^{d\prime}R^{d\prime\prime}$, $-NR^{d\prime\prime}SO_2R^{d\prime}$ $-CN$ and $-NO_2$.

Similarly, substituents for the aryl and heteroaryl groups are varied and selected from: -halo, $-OR^{e\prime}$, $-OC(O)R^{e\prime}$, $-NR^{e\prime}R^{e\prime\prime}$, $-SR^{e\prime}$, $-R^{e\prime}$, $-CN$, $-NO_2$, $-CO_2R^{e\prime}$, $-NR^{e\prime\prime}C(O)NR^{e\prime}R^{e\prime\prime}$, $-C(O)R^{e\prime}$, $-OC(O)NR^{e\prime}R^{e\prime\prime}$, $-NR^{e\prime\prime}C(O)R^{e\prime}$, $-NR^{e\prime\prime}CO_2R^{e\prime}$, $-NR^{e\prime\prime}C(O)NR^{e\prime}R^{e\prime\prime}$, $-NR^{e\prime\prime\prime}SO_2NR^{e\prime}R^{e\prime\prime}$, $-NHC(NH_2)=NH$, $-NR^{e\prime}C(NH_2)=NH$, $-NH-C(NH_2)=NR^{e\prime}$, $-S(O)R^{e\prime}$, $-SO_2R^{e\prime}$, $-SO_2NR^{e\prime}R^{e\prime\prime}$, $-NR^{e\prime\prime}SO_2R^{e\prime}$, $-N_3$, $-CH(Ph)_2$, perfluoroalkoxy and perfluoro$(C_1-C_4)$alkyl, in a number ranging from zero to the total number of open valences on the aromatic ring system.

$R^{e\prime}$, $R^{e\prime\prime}$ and $R^{e\prime\prime\prime}$ are independently selected from hydrogen, unsubstituted ($C_1$-$C_8$) alkyl, unsubstituted hetero($C_1$-$C_8$) alkyl, unsubstituted aryl, unsubstituted heteroaryl, unsubstituted aryl($C_1$-$C_4$) alkyl and unsubstituted aryloxy ($C_1$-$C_4$) alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Two of the substituents on adjacent atoms of an aryl or heteroaryl ring in an aryl or heteroaryl group as described herein may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -J-(CH$_2$)$_r$—K—, wherein J and K are independently —CH$_2$—, —O—, —NH—, —S—, —S(O)—, —S(O)$_2$—, —S(O)$_2$NR$^{fi}$- or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR$^{fi}$—, —S—, —S(O)—, —S(O)$_2$—, or —S(O)$_2$NR$^{a\prime}$—. The substituent R$^{fi}$ in —NR$^{fi}$— and —S(O)$_2$NR$^{fi}$— is selected from hydrogen or unsubstituted ($C_1$-$C_6$) alkyl.

"Stable compound" and "stable structure" are meant to indicate a compound that is sufficiently robust to survive isolation to a useful degree of purity from a reaction mixture, and formulation into an efficacious therapeutic agent.

As used herein the term "therapeutically effective amount" generally means the amount necessary to ameliorate at least one symptom of a disorder to be prevented, reduced, or treated as described herein. The phrase "therapeutically effective amount" as it relates to the GSNOR inhibitors of the present invention shall mean the GSNOR inhibitor dosage that provides the specific pharmacological response for which the GSNOR inhibitor is administered in a significant number of subjects in need of such treatment. It is emphasized that a therapeutically effective amount of a GSNOR inhibitor that is administered to a particular subject in a particular instance will not always be effective in treating the conditions/diseases described herein, even though such dosage is deemed to be a therapeutically effective amount by those of skill in the art. The phrase "therapeutically effective amount" as it relates to NK3 receptor antagonists of the present invention shall mean the NK3 receptor antagonist dosage that provides the specific pharmacological response for which the NK3 receptor antagonist is administered in a significant number of subjects in need of such treatment. It is emphasized that a therapeutically effective amount of a NK3 receptor antagonist that is administered to a particular subject in a particular instance will not always be effective in treating the conditions/diseases described herein, even though such dosage is deemed to be a therapeutically effective amount by those of skill in the art.

The term "biological sample" includes, but is not limited to, samples of blood (e.g., serum, plasma, or whole blood), urine, saliva, sweat, breast milk, vaginal secretions, semen, hair follicles, skin, teeth, bones, nails, or other secretions, body fluids, tissues, or cells. In accordance with the invention, the levels of the S-nitrosoglutathione reductase in the biological sample can be determined by the methods described in U.S. Patent Application Publication No. 2005/0014697.

D. Pharmaceutical Compositions

The invention encompasses pharmaceutical compositions comprising at least one compound of the invention described herein and at least one pharmaceutically acceptable carrier. Suitable carriers are described in "Remington: The Science and Practice, Twentieth Edition," published by Lippincott Williams & Wilkins, which is incorporated herein by reference. Pharmaceutical compositions according to the invention may also comprise one or more non-inventive compound active agents.

The pharmaceutical compositions of the invention can comprise novel compounds described herein, the pharmaceutical compositions can comprise known compounds which previously were not know to have GSNOR inhibitor activity or NK3 receptor antagonist activity, or a combination thereof.

The compounds of the invention can be utilized in any pharmaceutically acceptable dosage form, including but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the compounds of the invention described herein can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

For respiratory infections, an inhalation formulation can be used to achieve high local concentrations. Formulations suitable for inhalation include dry power or aerosolized or vaporized solutions, dispersions, or suspensions capable of being dispensed by an inhaler or nebulizer into the endobronchial or nasal cavity of infected patients to treat upper and lower respiratory bacterial infections.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent in the required amount in an appropriate solvent with one or a combination of ingredients enumerated above, as required, followed by filtered sterilization. Generally, dispersions are prepared by incorporating at least one compound of the invention into a sterile vehicle that contains a basic dispersion medium and any other required ingredients. In the case of sterile powders for the preparation of sterile injectable solutions, exemplary methods of preparation include vacuum drying and freeze-drying, both of which yield a powder of a compound of the invention plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the compound of the invention can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the compounds of the invention are prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the compounds of the invention may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of the compound of the invention calculated to produce the desired therapeutic effect in association with the required pharmaceutical carrier. The specification for the dosage unit forms of the invention are dictated by and directly dependent on the unique characteristics of the compound of the invention and the particular therapeutic effect to be achieved, and the limitations inherent in the art of compounding such an active agent for the treatment of individuals.

Pharmaceutical compositions according to the invention comprising at least one compound of the invention can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as Avicel® PH101 and Avicel® PH102, silicified microcrystalline cellulose (ProSolv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, such as Aerosil® 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet® (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

E. Kits Comprising the Compositions of the Invention

The present invention also encompasses kits comprising the compositions of the invention. Such kits can comprise, for example, (1) at least one compound of the invention; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus, such as an inhaler, nebulizer, syringe, etc.

F. Methods of Preparing Compounds of the Invention

The compounds of the invention can readily be synthesized using known synthetic methodologies or via a modification of known synthetic methodologies. As would be readily recognized by a skilled artisan, the methodologies described below allow the synthesis of dihydropyridin-2(1H)-ones having a variety of substituents. Exemplary synthetic methods are described in the examples below.

If needed, further purification and separation of enantiomers and diastereomers can be achieved by routine procedures known in the art. Thus, for example, the separation of enantiomers of a compound can be achieved by the use of chiral HPLC and related chromatographic techniques. Diastereomers can be similarly separated. In some instances, however, diastereomers can simply be separated physically, such as, for example, by controlled precipitation or crystallization.

The process of the invention, when carried out as prescribed herein, can be conveniently performed at temperatures that are routinely accessible in the art. In one embodiment, the process is performed at a temperature in the range of about 25° C. to about 110° C. In another embodiment, the temperature is in the range of about 40° C. to about 100° C. In yet another embodiment, the temperature is in the range of about 50° C. to about 95° C.

Synthetic steps that require a base are carried out using any convenient organic or inorganic base. Typically, the base is not nucleophilic. Thus, in one embodiment, the base is selected from carbonates, phosphates, hydroxides, alkoxides, salts of disilazanes, and tertiary amines.

The process of the invention, when performed as described herein, can be substantially complete after several minutes to after several hours depending upon the nature and quantity of reactants and reaction temperature. The determination of when the reaction is substantially complete can be conveniently evaluated by ordinary techniques known in the art such as, for example, HPLC, LCMS, TLC, and $^1$H NMR.

G. Methods of Treatment

The invention encompasses methods of preventing or treating (e.g., alleviating one or more symptoms of) medical conditions through use of one or more of the disclosed compounds. The methods comprise administering a therapeutically effective amount of a compound of the invention to a patient in need. The compositions of the invention can also be used for prophylactic therapy.

The compound of the invention used in the methods of treatment according to the invention can be: (1) a novel compound described herein, or a pharmaceutically acceptable salt thereof, a prodrug thereof, or a metabolite thereof; (2) a compound which was known prior to the present invention, but wherein it was not known that the compound is a GSNOR inhibitor or NK3 receptor antagonist, or a pharmaceutically acceptable salt thereof, a prodrug thereof, or a metabolite thereof; or (3) a compound which was known prior to the present invention, and wherein it was known that the compound is a GSNOR inhibitor or NK3 receptor antagonist, but wherein it was not known that the compound is useful for the methods of treatment described herein, or a pharmaceutically acceptable salt thereof, a prodrug thereof, or a metabolite thereof.

The patient can be any animal, domestic, livestock or wild, including, but not limited to cats, dogs, horses, pigs and cattle, and preferably human patients. As used herein, the terms patient and subject may be used interchangeably.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder. More specifically, "treating" includes reversing, attenuating, alleviating, minimizing, suppressing or halting at least one deleterious symptom or effect of a disease (disorder) state, disease progression, disease causative agent (e.g., bacteria or viruses), or other abnormal condition. Treatment is continued as long as symptoms and/or pathology ameliorate.

In general, the dosage, i.e., the therapeutically effective amount, ranges from 1 μg to 10 g/kg and often ranges from 10 μg to 1 g/kg or 10 μg to 100 mg/kg body weight of the subject being treated, per day.

H. GSNOR Uses

In subjects with deleteriously high levels of GSNOR or GSNOR activity, modulation may be achieved, for example, by administering one or more of the disclosed compounds that disrupts or down-regulates GSNOR function, or decreases GSNOR levels. These compounds may be administered with other GSNOR inhibitor agents, such as anti-GSNOR antibodies or antibody fragments, GSNOR antisense, iRNA, or small molecules, or other inhibitors, alone or in combination with other agents as described in detail herein.

The present invention provides a method of treating a subject afflicted with a disorder ameliorated by NO donor therapy. Such a method comprises administering to a subject a therapeutically effective amount of a GSNOR inhibitor.

The disorders can include pulmonary disorders associated with hypoxemia and/or smooth muscle constriction in the lungs and/or lung infection and/or lung injury (e.g., pulmonary hypertension, ARDS, asthma, pneumonia, pulmonary fibrosis/interstitial lung diseases, cystic fibrosis, COPD) cardiovascular disease and heart disease, including conditions such as hypertension, ischemic coronary syndromes, atherosclerosis, heart failure, glaucoma, diseases characterized by angiogenesis (e.g., coronary artery disease), disorders where there is risk of thrombosis occurring, disorders where there is risk of restenosis occurring, chronic inflammatory diseases (e.g., AID dementia and psoriasis), diseases where there is risk of apoptosis occurring (e.g., heart failure, atherosclerosis, degenerative neurologic disorders, arthritis and liver injury (e.g., ischemic or alcoholic)), impotence, obesity caused by eating in response to craving for food stroke, reperfusion injury (e.g., traumatic muscle injury in heart or lung or crush injury), and disorders where preconditioning of heart or brain for NO protection against subsequent ischemic events is beneficial.

In one embodiment, the compounds of the present invention or a pharmaceutically acceptable salt thereof, or a prodrug or metabolite thereof, can be administered in combination with an NO donor. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFκB. NO donors including S-nitroso, O-nitroso, C-nitroso and N-nitroso compounds and nitro derivatives thereof and metal NO complexes, but not excluding other NO bioactivity generating compounds, useful herein are described in "Methods in Nitric Oxide Research," Feelisch et al. eds., pages 71-115 (J. S., John Wiley & Sons, New York, 1996), which is incorporated herein by reference. NO donors which are C-nitroso compounds where nitroso is attached to a tertiary carbon which are useful herein include those described in U.S. Pat. No. 6,359,182 and in WO 02/34705. Examples of S-nitroso compounds, including S-nitrosothiols useful herein, include, for example, S-nitrosoglutathione, S-nitroso-N-acetylpenicillamine, S-nitroso-cysteine and ethyl ester thereof, S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin. Examples of other NO donors useful herein are sodium nitroprusside (nipride), ethyl nitrite, isosorbide, nitroglycerin, SIN 1 which is molsidomine, furoxamines, N-hydroxy (N-nitrosamine) and perfluorocarbons that have been saturated with NO or a hydrophobic NO donor.

The combination of a GSNOR inhibitor with R(+) enantiomer of amlodipine, a known NO releaser (Zhang X. P at al. 2002 J. Cardiovascular Pharmacology 39, 208-214) is also an embodiment of the present invention.

The present invention also provides a method of treating a subject afflicted with pathologically proliferating cells where the method comprises administering to said subject a therapeutically effective amount of an inhibitor of GSNOR. The inhibitors of GSNOR are the compounds as defined above, or a pharmaceutically acceptable salt thereof, or a prodrug or metabolite thereof, in combination with a pharmaceutically acceptable carrier. Treatment is continued as long as symptoms and/or pathology ameliorate.

In another embodiment, the pathologically proliferating cells can be pathologically proliferating microbes. The microbes involved can be those where GSNOR is expressed to protect the microbe from nitrosative stress or where a host cell infected with the microbe expresses the enzyme, thereby protecting the microbe from nitrosative stress. The term "pathologically proliferating microbes" is used herein to mean pathologic microorganisms including but not limited to pathologic bacteria, pathologic viruses, pathologic *Chlamydia*, pathologic protozoa, pathologic *Rickettsia*, pathologic fungi, and pathologic mycoplasmata. More detail on the applicable microbes is set forth at columns 11 and 12 of U.S. Pat. No. 6,057,367. The term "host cells infected with pathologic microbes" includes not only mammalian cells infected with pathologic viruses but also mammalian cells containing intracellular bacteria or protozoa, e.g., macrophages containing *Mycobacterium tuberculosis, Mycobacterium* leper (leprosy), or *Salmonella typhi* (typhoid fever).

In another embodiment, the pathologically proliferating cells can be pathologic helminths. The term "pathologic helminths" is used herein to refer to pathologic nematodes, pathologic trematodes and pathologic cestodes. More detail on the applicable helminths is set forth at column 12 of U.S. Pat. No. 6,057,367.

In another embodiment, the pathologically proliferating cells can be pathologically proliferating mammalian cells. The term "pathologically proliferating mammalian cells" as used herein means cells of the mammal that grow in size or number in said mammal so as to cause a deleterious effect in the mammal or its organs. The term includes, for example, the pathologically proliferating or enlarging cells causing restenosis, the pathologically proliferating or enlarging cells causing benign prostatic hypertrophy, the pathologically proliferating cells causing myocardial hypertrophy and proliferating cells at inflammatory sites such as synovial cells in arthritis or cells associated with a cell proliferation disorder.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration. The cell proliferative disorder can be a precancerous condition or cancer. The cancer can be primary cancer or metastatic cancer, or both.

As used herein, the term "cancer" includes solid tumors, such as lung, breast, colon, ovarian, pancreas, prostate, adenocarcinoma, squamous carcinoma, sarcoma, malignant glioma, leiomyosarcoma, hepatoma, head and neck cancer, malignant melanoma, non-melanoma skin cancers, as well as hematologic tumors and/or malignancies, such as leukemia, childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. In one embodiment, proliferative diseases include dysplasias and disorders of the like.

In one embodiment, the treating cancer comprises a reduction in tumor size, decrease in tumor number, a delay of tumor growth, decrease in metastaic lesions in other tissues or organs distant from the primary tumor site, an improvement in the survival of patients, or an improvement in the quality of patient life, or at least two of the above.

In another embodiment, the treating a cell proliferative disorder comprises a reduction in the rate of cellular proliferation, reduction in the proportion of proliferating cells, a decrease in size of an area or zone of cellular proliferation, or a decrease in the number or proportion of cells having an abnormal appearance or morphology, or at least two of the above.

In yet another embodiment, the compounds of the present invention or a pharmaceutically acceptable salt thereof, a prodrug thereof, or metabolite thereof, can be administered in combination with a second chemotherapeutic agent. In a further embodiment, the second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, araC, 5-fluorouracil, methotrexate, docetaxel, goserelin, vincristin, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

In one embodiment, the compounds of the present invention or a pharmaceutically acceptable salt thereof, a prodrug thereof, or metabolite thereof, can be administered in combination with an agent that imposes nitrosative or oxidative stress. Agents for selectively imposing nitrosative stress to inhibit proliferation of pathologically proliferating cells in combination therapy with GSNOR inhibitors herein and dosages and routes of administration therefor include those disclosed in U.S. Pat. No. 6,057,367, which is incorporated herein. Supplemental agents for imposing oxidative stress (i.e., agents that increase GSSG (oxidized glutathione) over GSH (glutathione) ratio or NAD(P) over NAD(P)H ratio or increase thiobarbituric acid derivatives) in combination therapy with GS-FDH inhibitors herein include, for example, L-buthionine-S-sulfoximine (BSO), glutathione reductase inhibitors (e.g., BCNU), inhibitors or uncouplers of mitochondrial respiration and drugs that increase reactive oxygen species (ROS), e.g., adriamycin, in standard dosages with standard routes of administration.

GSNOR inhibitors may also be co-administered with a phosphodiesterase inhibitor (e.g., rolipram, cilomilast, roflumilast, Viagra® (sildenifil citrate), Cialis® (tadalafil), Levitra® (vardenifil), etc.), a β-agonist, a steroid, or a leukotriene antagonist (LTD-4). Those skilled in the art can readily determine the appropriate therapeutically effective amount depending on the disorder to be ameliorated.

GSNOR inhibitors may be used as a means to improve β-adrenergic signaling. In particular, inhibitors of GSNOR alone or in combination with β-agonists could be used to treat or protect against heart failure, or other vascular disorders such as hypertension and asthma. GSNOR inhibitors can also be used to modulate G protein coupled receptors (GPCRs) by potentiating Gs G-protein, leading to smooth muscle relaxation (e.g., airway and blood vessels), and by attenuating Gq G-protein, and thereby preventing smooth muscle contraction (e.g., in airway and blood vessels).

The therapeutically effective amount for the treatment of a subject afflicted with a disorder ameliorated by NO donor therapy is the GSNOR inhibiting amount in vivo that causes amelioration of the disorder being treated or protects against a risk associated with the disorder. For example, for asthma, a therapeutically effective amount is a bronchodilating effective amount; for cystic fibrosis, a therapeutically effective amount is an airway obstruction ameliorating effective amount; for ARDS, a therapeutically effective amount is a hypoxemia ameliorating effective amount; for heart disease, a therapeutically effective amount is an angina relieving or angiogenesis inducing effective amount; for hypertension, a therapeutically effective amount is a blood pressure reducing effective amount; for ischemic coronary disorders, a therapeutic amount is a blood flow increasing effective amount; for atherosclerosis, a therapeutically effective amount is an endothelial dysfunction reversing effective amount; for glaucoma, a therapeutic amount is an intraocular pressure reducing effective amount; for diseases characterized by angiogenesis, a therapeutically effective amount is an angiogenesis inhibiting effective amount; for disorders where there is risk of thrombosis occurring, a therapeutically effective amount is a thrombosis preventing effective amount; for disorders where there is risk of restenosis occurring, a therapeutically effective amount is a restenosis inhibiting effective amount; for chronic inflammatory diseases, a therapeutically effective amount is an inflammation reducing effective amount; for disorders where there is risk of apoptosis occurring, a therapeutically effective amount is an apoptosis preventing effective amount; for impotence, a therapeutically effective is an erection attaining or sustaining effective amount; for obesity, a therapeutically effective amount is a satiety causing effective amount; for stroke, a therapeutically effective amount is a blood flow increasing or a TIA protecting effective amount; for reperfusion injury, a therapeutically effective amount is a function increasing effective amount; and for preconditioning of heart and brain, a therapeutically effective amount is a cell protective effective amount, e.g., as measured by triponin or CPK.

The therapeutically effective amount for the treatment of a subject afflicted with pathologically proliferating cells means a GSNOR inhibiting amount in vivo which is an antiproliferative effective amount. Such antiproliferative effective amount as used herein means an amount causing reduction in rate of proliferation of at least about 20%, at least about 10%, at least about 5%, or at least about 1%.

I. NK3 Uses

The compounds of Formula I, particularly the active enantiomers that antagonize the NK3 receptor are useful in the prevention and treatment of a wide variety of clinical conditions which are characterized by overstimulation of the tachkinin receptors, in particular, NK1, NK2 and NK3, and most particularly NK3. These conditions may include disorders of the central nervous system (CNS) such as anxiety, depression, psychosis, and schizophrenia; neurodegenerative disorders such as AIDS related dementia, senile dementia of the Alzheimer's type, Alzheimer's disease and Down's syndrome; demyelinating diseases such as multiple sclerosis and amyotrophic lateral sclerosis and other neuropathological disorders such as diabetic or peripheral neuropathy, AIDS related neuropathy, chemotherapy-induced neuropathy, and neuralgia; respiratory diseases such as chronic obstructive airways disease, bronchopneumonia, bronchospasm and asthma; inflammatory diseases such as inflammatory bowel disease, psoriasis, fibrositis, osteoarthritis, and rheumatoid arthritis;

allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczemoatoid dermatitis; addiction disorders such as alcoholism; stress related somatic disorders; reflex sympathetic dystrophy such as shoulder/had syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function; fibrosing and collagen diseases such as *scleroderma* and eosinophilic fascioliasis; disorders of blood flow caused by vasodilation and vasospastic diseases such as angina, migraine and Reynaud's disease; and pain or nociception, for example, that is attributable to or associated with any of the foregoing conditions especially the transmission of pain in migraine. Hence, these compounds are readily adapted to therapeutic use for the treatment of physiological disorders associated with the overstimulation of the tachykinin receptors, in particular NK1, NK2 and NK3, and most particularly NK3.

J. Uses in an Apparatus

The compounds of the present invention or a pharmaceutically acceptable salt thereof, or a prodrug or metabolite thereof, can be applied to various apparatus in circumstances when the presence of such compounds would be beneficial. Such apparatus can be any device or container, for example, implantable devices in which a compound of the invention can be used to coat a surgical mesh or cardiovascular stent prior to implantation in a patient. The compounds of the invention can also be applied to various apparatus for in vitro assay purposes or for culturing cells.

The compounds of the present invention or a pharmaceutically acceptable salt thereof, or a prodrug or metabolite thereof, can also be used as an agent for the development, isolation or purification of binding partners to compounds of the invention, such as antibodies, natural ligands, and the like. Those skilled in the art can readily determine related uses for the compounds of the present invention.

EXAMPLES

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

Examples 1-17 list representative novel dihydropyridin-2 (1H)-one analogs of Formula I useful as GSNOR inhibitors and NK3 antagonists of the invention. The synthetic methods that can be used to prepare each compound are detailed in Examples 1-17. In some cases, the starting material was not commercially available. In these cases, the synthesis of the intermediates is described in Example 18. Supporting mass spectrometry data and proton NMR data for each compound is also included in Examples 1-17.

Example 1

Compound 1, 4-(3-ethoxy-4-hydroxy-5-nitrophenyl)-5,6-diphenyl-3,4-dihydropyridin-2(1H)-one

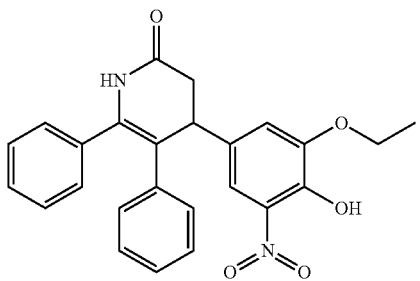 [SMILES: CCOc1cc(C2CC(=O)NC(c3ccccc3)=C2c2ccccc2)cc([N+](=O)[O-])c1O]

A mixture of 1,2-diphenylethanone (150 mg, 0.76 mmol), 3-ethoxy-4-hydroxy-5-nitrobenzaldehyde (194 mg, 0.92 mmol), meldrum's acid (132 mg, 0.92 mmol) and ammonium acetate (71 mg, 0.92 mmol) in acetic acid (5 mL) was refluxed overnight. The solvent was removed under reduced pressure and the residue was purified by silica gel column chromatography (EtOAc: PE=2:1) and prep-HPLC (0.1% TFA as additive) to afford Compound 1 as yellow solid (40 mg, yield: 13%). $^1$H NMR (DMSO-$d_6$ 300 MHz): δ 10.20 (s, 1H), 9.60 (s, 1H), 7.47 (d, J=3.0 Hz, 1H), 7.24-7.18 (m, 6H), 7.01-6.96 (m, 3H), 6.79 (d, J=8.1 Hz, 2H), 4.06 (q, J=6.0 Hz, 2H), 3.96 (d, J=5.1 Hz, 1H), 3.14-3.07 (m, 2H), 1.31 (t, J=7.2 Hz, 3H); MS (ESI): m/z 430.9 [M+H$^+$].

Example 2

Compound 2, 4-(3-ethoxy-4-hydroxy-5-nitrophenyl)-6-(pyridin-3-yl)-5-(thiophen-3-yl)-3,4-dihydropyridin-2(1H)-one

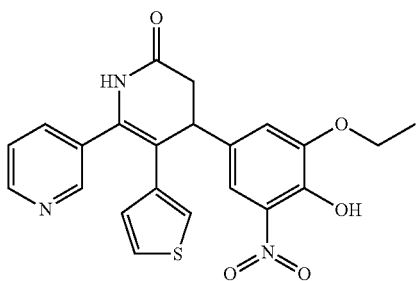 [SMILES: CCOc1cc(C2CC(=O)NC(c3cccnc3)=C2c2ccsc2)cc([N+](=O)[O-])c1O]

A mixture of 1-(pyridin-3-yl)-2-(thiophen-3-yl)ethanone (Intermediate 1, see Example 18 for synthesic description of all intermediates) (230 mg, 1.1 mmol), 3-ethoxy-4-hydroxy-5-nitrobenzaldehyde (296 mg, 1.4 mmol), meldrum's acid (202 mg, 1.4 mmol) and AcONH$_4$ (108 mg, 1.4 mmol) in AcOH (3 mL) was refluxed under N$_2$ overnight. The mixture was concentrated under reduced pressure and the residue was purified by prep-HPLC (0.1% TFA as additive) to give Compound 2 (60 mg, 12%). $^1$H NMR (MeOD 400 MHz): δ 8.70 (d, J=5.2 Hz, 1H), 8.67 (s, 1H), 8.30 (d, J=8.0 Hz, 1H), 7.90-7.62 (m, 1H), 7.72-7.60 (m, 1H), 7.27-7.24 (m, 2H), 6.94-6.92 (m, 1H), 6.58 (d, J=4.8 Hz, 1H), 4.20-4.11 (m, 3H), 3.30-3.25 (m, 1H), 2.79-2.74 (dd, J=16.2, 3.2 Hz, 1H), 1.45 (t, J=6.8 Hz, 3H). MS (ESI): m/z 438.3 [M+1]+.

Example 3

Compound 3, 4-(4-(2H-tetrazol-5-yl)phenyl)-5-phenyl-6-(pyridin-3-yl)-3,4-dihydropyridin-2(1H)-one

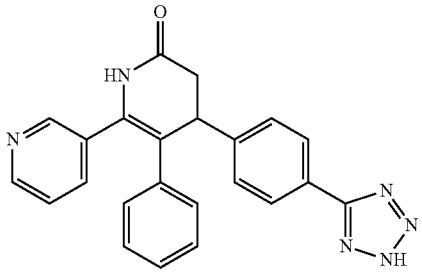 [SMILES: O=C1CC(c2ccc(-c3nn[nH]n3)cc2)C(c2ccccc2)=C(c2cccnc2)N1]

A mixture of 2-phenyl-1-(pyridin-3-yl)ethanone (Intermediate 2) (100 mg, 0.50 mmol), 4-(2H-tetrazol-5-yl)benzaldehyde (500 mg), meldrum's acid (88 mg, 0.61 mmol) and NH4OAc (47 mg, 0.61 mmol) in AcOH (5 mL) was refluxed under N2 overnight. The mixture was concentrated under reduced pressure and purified by prep-HPLC (0.1% TFA as additive) to give Compound 3 (25 mg, yield 13%) as yellow solid. $^1$H NMR (CD$_3$OD 400 MHz): δ 8.68-8.50 (m, 2H), 8.21-8.15 (m, 1H), 8.10-8.00 (m, 2H), 7.75-7.60 (m, 3H), 7.20-7.05 (m, 3H), 7.03-6.88 (m, 2H), 4.31-4.20 (m, 1H), 3.45-3.30 (m, 1H), 2.83-2.71 (m, 1H). MS (ESI): m/z 395.4 [M+1]+.

Example 4

Compound 4, 4-(3-ethoxy-4-hydroxy-5-nitrophenyl)-6-(1-methyl-1H-pyrazol-4-yl)-5-(thiophen-3-yl)-3,4-dihydropyridin-2(1H)-one

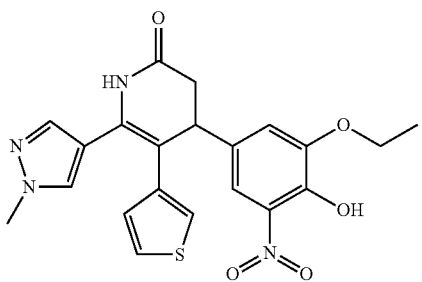 [SMILES: CCOc1cc(C2CC(=O)NC(c3cnn(C)c3)=C2c2ccsc2)cc([N+](=O)[O-])c1O]

A mixture of 1-(1-methyl-1H-pyrazol-4-yl)-2-(thiophen-3-yl)ethanone (Intermediate 3) (150 mg, 0.73 mmol), 3-ethoxy-4-hydroxy-5-nitrobenzaldehyde (185 mg, 0.87 mmol), meldrum's acid (125 mg, 0.87 mmol) and AcONH4 (84 mg, 1.1 mmol) in AcOH (3 mL) was refluxed under N2 overnight. The mixture was concentrated under reduced pressure and the residue was purified by prep-HPLC (0.1% TFA as additive) to give Compound 4 as yellow solid (20 mg, 6%). $^1$H NMR (DMSO-d6, 400 MHz): δ 10.20 (s, 1H), 9.43 (s, 1H), 7.62 (s, 1H), 7.42-7.36 (m, 2H), 7.19-7.11 (m, 1H), 7.06 (s, 2H), 6.70-6.68 (m, 1H), 4.11-4.03 (m, 2H), 3.95-3.92 (m, 1H), 3.77 (s, 3H), 3.08 (dd, J=16.4, 7.6 Hz, 1H), 2.60-2.52 (m, 1H), 1.34 (t, J=6.8 Hz, 3H). MS (ESI): m/z 440.9 [M+1]+.

Example 5

Compound 5, 4-(4-(2H-tetrazol-5-yl)phenyl)-6-(1-methyl-1H-pyrazol-4-yl)-5-(thiophen-3-yl)-3,4-dihydropyridin-2(1H)-one

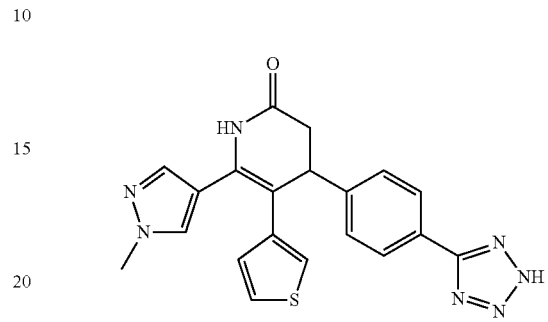

A mixture of 1-(1-methyl-1H-pyrazol-4-yl)-2-phenylethanone (Intermediate 4) (400 mg, 2.0 mmol), 4-(2H-tetrazol-5-yl)benzaldehyde (420 mg, 2.4 mmol), meldrum's acid (345 mg, 2.4 mmol) and AcONH4 (185 mg, 2.4 mmol) in AcOH (4 mL) was refluxed under N2 overnight. The mixture was concentrated in vacuo and the residue was purified by prep-HPLC (0.1% TFA as additive) to give Compound 5 (25 mg, 3%). $^1$H NMR (DMSO-d6 400 MHz): δ 9.46 (brs, 1H), 7.98 (d, J=8.0 Hz, 2H), 7.58-7.48 (m, 3H), 7.25-7.16 (m, 3H), 7.15 (d, J=6.4 Hz, 2H), 6.91 (s, 1H), 4.00 (d, J=5.2 Hz, 1H), 3.72 (s, 3H), 3.20 (dd, J=16.0 Hz, 7.6 Hz, 1H), 2.50-2.45 (m, 1H). MS (ESI): m/z 398.0 [M+1]+.

Example 6

Compound 6, 2-hydroxy-4-(2-oxo-5,6-diphenyl-1,2,3,4-tetrahydropyridin-4-yl)benzoic acid

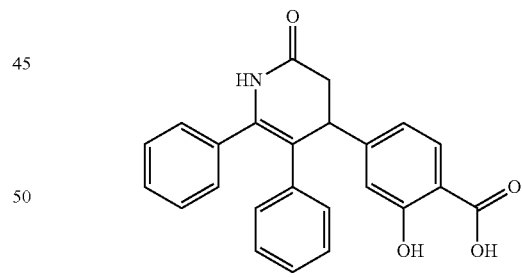

A mixture of 1,2-diphenylethanone (800 mg, 4.0 mmol), meldrum's acid (692 mg, 4.8 mmol), methyl 4-formyl-2-hydroxybenzoate (Intermediate 5) (742 mg, 4.0 mmol) and NH4OAc (370 mg, 4.8 mmol) in AcOH (10 mL) was refluxed under N2 overnight. The mixture was concentrated under reduced pressure and the residue was taken up in MeOH (10 mL) and aq. NaOH (2 M, 10 mL) and was stirred at 60° C. under N2 for 6 hours. The resulting mixture was cooled to room temperature, and then acidified with aqueous HCl (2 M) to pH=4, extracted with ethyl acetate (50 mL×3). The combined organic layers were dried over anhydrous Na2SO4 and concentrated under reduced pressure. The residue was purified by prep-HPLC (0.1% TFA as additive) to give Compound 6 (195 mg, 2-step yield 12%) as off-white solid. ¹H NMR (DMSO-d6 400 MHz): δ 11.29 (brs, 1H), 9.63 (brs, 1H), 7.79 (d, J=8.4 Hz, 1H), 7.36-7.22 (m, 5H), 7.10-6.98 (m, 5H), 6.86-6.79 (m, 2H), 4.00 (d, J=6.0 Hz, 1H), 3.21 (dd, J=16.0, 7.6 Hz, 1H), 2.49-2.41 (m, 1H). MS (ESI): m/z 385.7 [M+1]⁺.

Example 7

Compound 7, 2-hydroxy-4-(2-oxo-6-phenyl-5-(thiophen-3-yl)-1,2,3,4-tetrahydropyridin-4-yl)benzoic acid

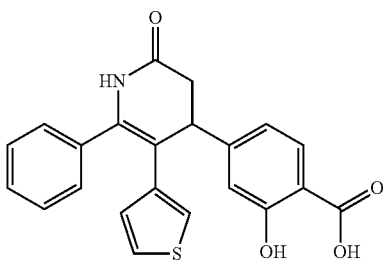 [SMILES: O=C1CC(c2ccc(C(=O)O)c(O)c2)C(c2ccsc2)=C(c2ccccc2)N1]

To a mixture of 1-phenyl-2-(thiophen-3-yl)ethanone (Intermediate 6) (300 mg, 1.5 mmol), methyl 4-formyl-2-hydroxybenzoate (Intermediate 5) (325 mg, 1.8 mmol), meldrum's acid (260 mg, 1.8 mmol) and AcONH₄ (140 mg, 1.8 mmol) in AcOH (3 mL) was refluxed overnight. The mixture was concentrated in vacuo and the residue was taken up in MeOH (10 mL) and aq. NaOH (2 M, 10 mL) and was stirred at 40° C. overnight. The resulting mixture was cooled to room temperature, and then acidified with aq. HCl (2 M, 12 mL) to pH=5. Followed a standard aqueous/EtOAc workup i.e. the mixture was extracted with EtOAc (3 times), washed with brine, then combined organic layers were dried over anhydrous Na₂SO₄ and concentrated in vacuo. The residue was purified by prep-HPLC (0.1% TFA as additive) to give Compound 7 (25 mg, 2-steps yield 4%) as yellow solid. ¹H NMR (DMSO-d6 400 MHz): δ 9.60 (s, 1H), 7.78 (d, J=8.0 Hz, 1H), 7.44-7.36 (m, 3H), 7.35-7.26 (m, 3H), 7.22-7.15 (m, 1H), 7.14-6.98 (m, 2H), 6.82-6.74 (m, 1H), 6.25 (d, J=4.8 Hz, 1H), 4.13-4.05 (m, 1H), 3.18 (dd, J=16.2, 8.0 Hz, 1H), 2.46-2.42 (m, 1H). MS (ESI): m/z 391.7 [M+1]⁺.

Example 8

Compound 8, 4-(4-(2H-tetrazol-5-yl)phenyl)-6-(1-methyl-1H-pyrazol-4-yl)-5-phenyl-3,4-dihydropyridin-2(1H)-one

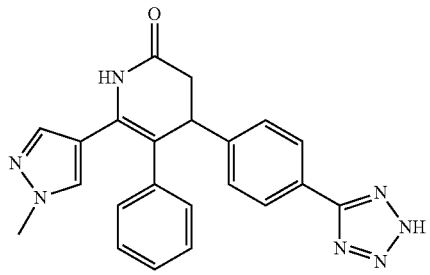 [SMILES: Cn1cc(C2=C(c3ccccc3)C(c3ccc(-c4nn[nH]n4)cc3)CC(=O)N2)cn1]

A mixture of 1-(1-methyl-1H-pyrazol-4-yl)-2-phenylethanone (Intermediate 4) (400 mg, 2.0 mmol), 4-(2H-tetrazol-5-yl)benzaldehyde (420 mg, 2.4 mmol), meldrum's acid (345 mg, 2.4 mmol) and AcONH₄ (185 mg, 2.4 mmol) in AcOH (4 mL) was refluxed under N₂ overnight. The mixture was concentrated in vacuo and the residue was purified by prep-HPLC (0.1% TFA as additive) to give Compound 8 (25 mg, 3%). ¹H NMR (DMSO-d6 400 MHz): δ 9.46 (brs, 1H), 7.98 (d, J=8.0 Hz, 2H), 7.58-7.48 (m, 3H), 7.25-7.16 (m, 3H), 7.15 (d, J=6.4 Hz, 2H), 6.91 (s, 1H), 4.00 (d, J=5.2 Hz, 1H), 3.72 (s, 3H), 3.20 (dd, J=16.0, 7.6 Hz, 1H), 2.50-2.45 (m, 1H). MS (ESI): m/z 398.0 [M+1]⁺.

Example 9

Compound 9, 2-hydroxy-4-(6-(1-methyl-1H-pyrazol-4-yl)-2-oxo-5-(thiophen-3-yl)-1,2,3,4-tetrahydropyridin-4-yl)benzoic acid

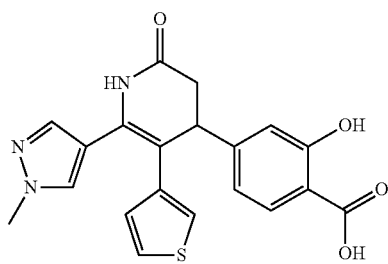 [SMILES: Cn1cc(C2=C(c3ccsc3)C(c3ccc(C(=O)O)c(O)c3)CC(=O)N2)cn1]

A mixture of 1-(1-methyl-1H-pyrazol-4-yl)-2-(thiophen-3-yl)ethanone (Intermediate 3) (300 mg, 1.5 mmol), methyl 4-formyl-2-hydroxybenzoate (Intermediate 5) (315 mg, 1.7 mmol), meldrum's acid (245 mg, 1.7 mmol) and AcONH₄ (130 mg, 1.7 mmol) in AcOH (3 mL) was refluxed under N₂ atmosphere overnight. The mixture was concentrated under reduced pressure and taken up in MeOH (10 mL) and aq. NaOH (2 M, 10 mL). The reaction was stirred at 40° C. for 5 hours. The resulting mixture was cooled to room temperature, and then acidified with aq. HCl (2 M, 12 mL) to pH=5, followed by a standard aqueous/EtOAc workup. The residue was purified by prep-HPLC (0.1% TFA as additive) to give Compound 9 as a gray solid (45 mg, 2-steps yield 8%). ¹H NMR (DMSO-d6 400 MHz): δ 11.24 (brs, 1H), 9.41 (brs, 1H), 7.73 (d, J=8.4 Hz, 1H), 7.63 (s, 1H), 7.38 (dd, J=4.8, 2.8 Hz, 1H), 7.08 (s, 1H), 7.03 (d, J=1.6 Hz, 1H), 6.90-6.82 (m, 2H), 6.67 (d, J=5.2 Hz, 1H), 3.94 (d, J=6.4 Hz, 1H), 3.77 (s, 3H), 3.12 (dd, J=16.0, 7.6 Hz, 1H), 2.48-2.38 (m, 1H). MS (ESI): m/z 395.9 [M+1]⁺.

Example 10

Compound 10, 2-fluoro-6-hydroxy-4-(2-oxo-5,6-diphenyl-1,2,3,4-tetrahydropyridin-4-yl)benzoic acid

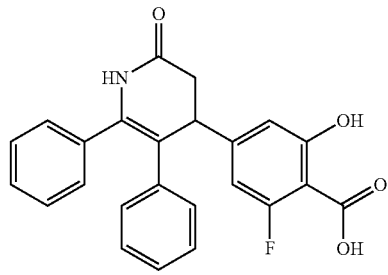 [SMILES: O=C1CC(c2cc(O)c(C(=O)O)c(F)c2)C(c2ccccc2)=C(c2ccccc2)N1]

A mixture of 1, 2-diphenyl-ethanone (250 mg, 1.3 mmol), methyl 2-fluoro-4-formyl-6-hydroxybenzoate (Intermediate 7) (252 mg, 1.3 mmol), meldrum's acid (230 mg, 1.6 mmol) and NH$_4$OAc (125 mg, 1.6 mmol) in AcOH (5 mL) was refluxed under N$_2$ overnight. The mixture was concentrated in vacuo and the residue was taken up in MeOH (5 mL) and aq. NaOH (2 M, 5 mL). This was stirred at 60° C. under N$_2$ for 5 hours. The resulting mixture was cooled to room temperature, and then acidified with aqueous HCl (2 M) to pH=4, followed by a standard aqueous/EtOAc workup. The residue was purified by prep-HPLC (0.1% TFA as additive) to give Compound 10 (28 mg, 2-step yield 5%) as gray solid. $^1$H NMR (DMSO-d$_6$ 400 MHz): δ 9.64 (brs, 1H), 7.24-7.21 (m, 5H), 7.12-6.98 (m, 3H), 6.88-6.78 (m, 3H), 6.74 (d, J=11.2 Hz, 1H), 4.01-3.90 (m, 1H), 3.20 (dd, J=16.4, 7.6 Hz, 1H), 2.49-2.41 (m, 1H). MS (ESI): m/z 403.9 [M+1]$^+$.

Example 11

Compound 11, 2-fluoro-6-hydroxy-4-(6-(1-methyl-1H-pyrazol-4-yl)-2-oxo-5-(thiophen-3-yl)-1,2,3,4-tetrahydropyridin-4-yl)benzoic acid

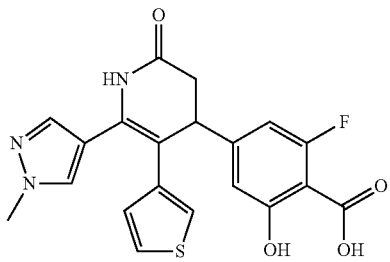 [SMILES: Cn1cc(C2=C(c3ccsc3)C(c3cc(O)c(C(=O)O)c(F)c3)CC(=O)N2)cn1]

A mixture of 1-(1-methyl-1H-pyrazol-4-yl)-2-(thiophen-3-yl)ethanone (Intermediate 3) (250 mg, 1.2 mmol), methyl 2-fluoro-4-formyl-6-hydroxybenzoate (Intermediate 7) (240 mg, 1.2 mmol), meldrum's acid (217 mg, 1.5 mmol) and NH$_4$OAc (116 mg, 1.5 mmol) in AcOH (5 mL) was refluxed under N$_2$ overnight. The mixture was concentrated under reduced pressure and the residue was taken up in MeOH (5 mL) and 2M NaOH (5 mL). The reaction was stirred at 60° C. under N$_2$ for 5 hours. After being cooled to room temperature, the mixture was acidified with aqueous HCl (2 M) to pH=4 followed by a standard aqueous/EtOAc workup. The residue was purified by prep-HPLC (0.1% TFA as additive) to give Compound 11 (14 mg, 2-step yield 2%) as gray solid. $^1$H NMR (DMSO-d$_6$ 400 MHz): δ 9.42 (brs, 1H), 7.63 (s, 1H), 7.39 (dd, J=4.8, 3.2 Hz, 1H), 7.10 (s, 1H), 7.06 (d, J=2.8 Hz, 1H), 6.75-6.55 (m, 3H), 3.90 (d, J=6.4 Hz, 1H), 3.77 (s, 3H), 3.10 (dd, J=16.0, 7.6 Hz, 1H), 2.49-2.38 (m, 1H). MS (ESI): m/z 413.8 [M+1]$^+$.

Example 12

Compound 12, 2-ethoxy-6-hydroxy-4-(2-oxo-5,6-diphenyl-1,2,3,4-tetrahydropyridin-4-yl)benzoic acid

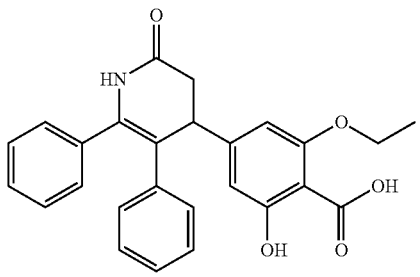 [SMILES: CCOc1cc(C2CC(=O)NC(c3ccccc3)=C2c2ccccc2)cc(O)c1C(=O)O]

A mixture of 1,2-diphenylethanone (216 mg, 1.1 mmol), methyl 2-ethoxy-4-formyl-6-hydroxybenzoate (Intermediate 8) (304 mg, 1.3 mmol), meldrum's acid (260 mg, 1.8 mmol) and NH$_4$OAc (140 mg, 1.8 mmol) in HOAc (5 mL) was refluxed under N$_2$ atmosphere overnight. The mixture was concentrated under reduced pressure and the resulting residue was taken up in MeOH (10 mL) and aq. NaOH (2 M, 10 mL). The reaction was stirred at 70° C. under N$_2$ overnight. The resulting mixture was cooled to room temperature, and then acidified with aqueous HCl (2 M) to pH=3, followed by a standard aqueous/EtOAc workup. The residue was purified by prep-HPLC (0.1% TFA as additive) to give Compound 12 (22 mg, 2-step yield 5%) as off-white solid. $^1$H NMR (CD$_3$OD 400 MHz): δ 7.36-7.26 (m, 5H), 7.10-7.03 (m, 3H), 6.96-6.90 (m, 2H), 6.73 (d, J=0.8 Hz, 1H), 6.67 (s, 1H), 4.24 (q, J=7.2 Hz, 2H), 4.02 (dd, J=7.6, 2.4 Hz, 1H), 3.35-3.25 (m, 1H), 2.68 (dd, J=16.0, 2.8 Hz, 1H), 1.46 (t, J=7.2 Hz, 3H). MS (ESI): m/z 429.8 [M+1]$^+$.

Example 13

Compound 13, 4-(6-cyclohexyl-2-oxo-5-(thiophen-3-yl)-1,2,3,4-tetrahydropyridin-4-yl)-2-fluoro-6-hydroxybenzoic acid

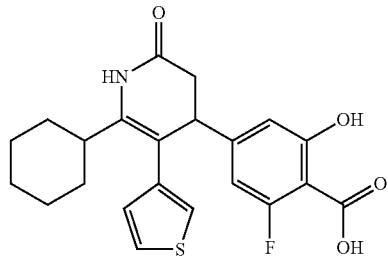 [SMILES: O=C1CC(c2cc(O)c(C(=O)O)c(F)c2)C(c2ccsc2)=C(C2CCCCC2)N1]

A mixture of 1-cyclohexyl-2-(thiophen-3-yl)ethanone (Intermediate 9) (271 mg, 1.3 mmol), methyl 2-fluoro-4-formyl-6-hydroxybenzoate (Intermediate 7) (300 mg, 1.5 mmol), meldrum's acid (216 mg, 1.5 mmol) and NH$_4$OAc (116 mg, 1.5 mmol) in HOAc (5 mL) was refluxed under N$_2$ overnight. The mixture was concentrated under reduced pressure and the residue was taken up in MeOH (10 mL) and aq. NaOH (2 M, 10 mL). The reaction was stirred at 50° C. under N$_2$ overnight. The resulting mixture was cooled, and then acidified with aqueous HCl (2 M) to pH=3, followed by a standard aqueous/EtOAc workup. The residue was purified by prep-HPLC (0.1% TFA as additive) to give Compound 13 (48 mg, 2-step yield 9%) as off-white solid. $^1$H NMR (CD$_3$OD 400 MHz): δ 7.38 (dd, J=5.2 Hz, 2.8 Hz, 1H), 7.08 (d, J=2.4 Hz, 1H), 6.92 (d, J=3.2 Hz, 1H), 6.66 (s, 1H), 6.53 (d, J=11.6 Hz, 1H), 3.84 (d, J=6.4 Hz, 1H), 3.11 (dd, J=16.4, 8.0 Hz, 1H), 2.76-2.66 (m, 1H), 2.54 (dd, J=16.4, 2.0 Hz, 1H), 1.92-1.52 (m, 7H), 1.38-1.18 (m, 3H). MS (ESI): m/z 415.8 [M+1]$^+$.

Example 14

Compound 14, 4-(4-hydroxy-3-(2-hydroxyethoxy)-5-nitrophenyl)-5,6-diphenyl-3,4-dihydropyridin-2(1H)-one

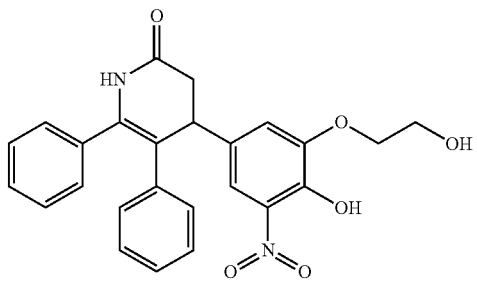 [SMILES: O=C1CC(c2cc(OCCO)c(O)c([N+](=O)[O-])c2)C(c2ccccc2)=C(c2ccccc2)N1]

A mixture of 1,2-diphenylethanone (300 mg, 1.5 mmol), 4-hydroxy-3-(2-hydroxyethoxy)-5-nitrobenzaldehyde (350 mg, 1.5 mmol), meldrum's acid (220 mg, 1.8 mmol) and NH$_4$OAc (140 mg, 1.8 mmol) in AcOH (5 mL) was refluxed under N$_2$ overnight. The mixture was concentrated under reduced pressure and the residue was taken up in MeOH (5 mL) and potassium carbonate (400 mg, 3.0 mmol) was added. The reaction was stirred at 25° C. for 2 hours. The mixture was poured into water, acidified with aqueous HCl (2 M) to pH=4, followed by a standard aqueous/EtOAc workup. The residue was purified by prep.-HPLC (0.1% TFA as additive) to give Compound 14 (36 mg, 2-step yield 6%) as yellow solid. $^1$H NMR (DMSO-d6 400 MHz): δ 9.62 (brs, 1H), 7.52 (s, 1H), 7.36-7.17 (m, 6H), 7.10-6.96 (m, 3H), 6.85 (d, J=6.8 Hz, 2H), 4.10-4.04 (m, 2H), 4.00 (d, J=5.6 Hz, 1H), 3.76 (t, J=4.8 Hz, 2H), 3.17 (dd, J=16.4, 7.2 Hz, 1H), 2.55 (m, 1H). MS (ESI): m/z 446.8 [M+1]$^+$.

Example 15

Compound 15, 2-fluoro-6-hydroxy-4-(1-methyl-2-oxo-5,6-diphenyl-1,2,3,4-tetrahydropyridin-4-yl)benzoic acid

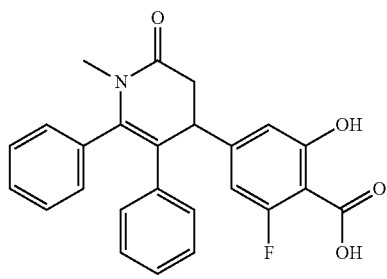 [SMILES: CN1C(=O)CC(c2cc(O)c(C(=O)O)c(F)c2)C(c2ccccc2)=C1c1ccccc1]

Step 1: Synthesis of methyl 2-fluoro-6-hydroxy-4-(2-oxo-5,6-diphenyl-1,2,3,4-tetrahydropyridin-4-yl)benzoate A mixture of 1,2-diphenylethanone (300 mg, 1.5 mmol), methyl 2-fluoro-4-formyl-6-hydroxybenzoate (Intermediate 7) (300 mg, 1.5 mmol), meldrum's acid (260 mg, 1.8 mmol) and NH$_4$OAc (140 mg, 1.8 mmol) in AcOH (5 mL) was refluxed under N$_2$ overnight. The mixture was concentrated under reduced pressure and the residue was purified by silica gel chromatography (PE:EtOAc=5:1) to give product (90 mg, 16%) as a yellow solid.

Step 2: Synthesis of methyl 2-fluoro-6-(methoxymethoxy)-4-(2-oxo-5,6-diphenyl-1,2,3,4-tetrahydropyridin-4-yl)benzoate To a mixture of the above product (90 mg, 0.22 mmol) and potassium carbonate (91 mg, 0.66 mmol) in DMF (5 mL) was added chloro(methoxy)methane (35 mg, 0.44 mmol) at 25° C. and stirred for 2 hours. Followed a standard aqueous/EtOAc workup to give product (90 mg, 91%).

Step 3: Synthesis of methyl 2-fluoro-6-(methoxymethoxy)-4-(1-methyl-2-oxo-5,6-diphenyl-1,2,3,4-tetrahydropyridin-4-yl)benzoate To a mixture of the above product (90 mg, 0.20 mmol) and potassium carbonate (80 mg, 0.60 mmol) in DMF (5 mL) was added iodomethane (57 mg, 0.40 mmol) at 25° C. and stirred for 2 hours. A standard aqueous/EtOAc workup was followed to give product (90 mg, 97%), which was used directly to the next step without further purification.

Step 4: Synthesis of 2-fluoro-6-hydroxy-4-(1-methyl-2-oxo-5,6-diphenyl-1,2,3,4-tetrahydropyridin-4-yl)benzoic acid A mixture of the above product in MeOH (5 mL) and 2N NaOH (5 mL) was stirred at 60° C. under N₂ atmosphere for 5 hours. After being cooled to room temperature, the mixture was acidified with aqueous HCl (2 M) to pH=4, followed by a standard aqueous/EtOAc workup. The residue was dissolved in MeOH (10 mL) and conc. HCl (0.5 mL) was added. After being stirred at 25° C. for 2 hours, the mixture was concentrated under reduced pressure. The residue was purified by prep.-HPLC (0.1% TFA as additive) to give Compound 15 (25 mg, yield 29%) as white solid. $^1$H NMR (DMSO-$d_6$ 400 MHz): δ 7.40-7.26 (m, 5H), 7.08-6.97 (m, 3H), 6.89 (s, 1H), 6.80-6.74 (m, 3H), 3.85 (dd, J=6.4, 2.0 Hz, 1H), 3.28 (dd, J=16.0, 7.2 Hz, 1H), 2.68 (s, 3H), 2.60 (dd, J=15.6, 2.4 Hz, 1H). MS (ESI): m/z 417.7 [M+1]$^+$.

Example 16

Compound 16, 4-(3-ethoxy-4-hydroxy-5-nitrophenyl)-1-methyl-5,6-diphenyl-3,4-dihydropyridin-2(1H)-one

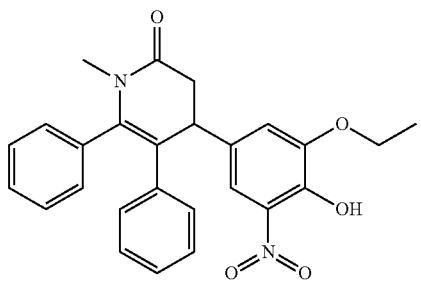 [SMILES: CCOc1cc(C2CC(=O)N(C)C(c3ccccc3)=C2c2ccccc2)cc([N+](=O)[O-])c1O]

Step 1: Synthesis of 4-(3-ethoxy-4-(methoxymethoxy)-5-nitrophenyl)-5,6-diphenyl-3,4-dihydropyridin-2(1H)-one To a mixture of 4-(3-ethoxy-4-hydroxy-5-nitrophenyl)-5,6-diphenyl-3,4-dihydropyridin-2(1H)-one (Compound 1, see Example 1) (200 mg, 0.47 mmol) and potassium carbonate (130 mg, 0.93 mmol) in DMF (5 mL) was added chloro(methoxy)methane (75 mg, 0.93 mmol) at 25° C. and then the mixture was stirred at the same temperature for 2 hours. The mixture was poured into water and a standard aqueous/EtOAc workup was followed to give product (200 mg, 98%).

Step 2: Synthesis of 4-(3-ethoxy-4-(methoxymethoxy)-5-nitrophenyl)-1-methyl-5,6-diphenyl-3,4-dihydropyridin-2(1H)-one To a mixture of the above compound (200 mg, 0.42 mmol) and potassium carbonate (580 mg, 4.2 mmol) in DMF (5 mL) was added iodomethane (600 mg, 4.2 mmol) at 25° C. and then the mixture was stirred for 2 hours. The mixture was poured into water and a standard aqueous/EtOAc workup was followed to give product (200 mg, 97%).

Step 3: Synthesis of 4-(3-ethoxy-4-hydroxy-5-nitrophenyl)-1-methyl-5,6-diphenyl-3,4-dihydropyridin-2(1H)-one To a mixture of the above compound in MeOH (10 mL) was added conc. HCl (0.5 mL), then the mixture was stirred at 25° C. for 2 hours. The mixture was concentrated under reduced pressure. The residue was purified by prep.-HPLC (0.1% TFA as additive) to give Compound 16 (120 mg, yield 66%) as yellow solid. $^1$H NMR (DMSO-$d_6$ 400 MHz): δ 7.52 (d, J=1.6 Hz, 1H), 7.48-7.39 (m, 3H), 7.38-7.24 (m, 3H), 7.06-6.98 (m, 3H), 6.79 (d, J=6.4 Hz, 2H), 4.20-4.08 (m, 2H), 3.96-3.88 (m, 1H), 3.25 (dd, J=16.0, 6.4 Hz, 1H), 2.68 (s, 3H), 2.65 (d, J=4.0 Hz, 1H), 1.37 (t, J=7.2 Hz, 3H). MS (ESI): m/z 444.8 [M+1]$^+$.

Example 17

Compound 17, 2-fluoro-6-hydroxy-4-(6-(1-methyl-1H-pyrazol-4-yl)-2-oxo-5-(thiophen-2-yl)-1,2,3,4-tetrahydropyridin-4-yl)benzoic acid

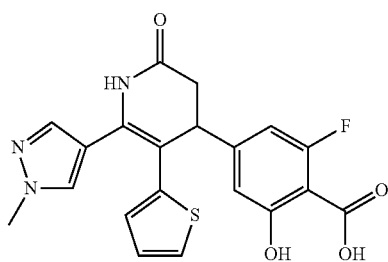 [SMILES: Cn1cc(C2=C(c3cccs3)C(c3cc(O)c(C(=O)O)c(F)c3)CC(=O)N2)cn1]

A mixture of 1-(1-methyl-1H-pyrazol-4-yl)-2-(thiophen-2-yl)ethanone (Intermediate 12) (250 mg, 1.20 mmol), 2-fluoro-4-formyl-6-hydroxybenzoic acid (Intermediate 11), meldrum's acid (202 mg, 1.40 mmol) and NH₄OAc (108 mg, 1.40 mmol) in AcOH (5 mL) was refluxed under N₂ overnight. The reaction was poured into water and a standard aqueous/EtOAc workup was followed. The residue was purified by prep. HPLC (0.1% TFA as additive) to give compound 17 (17 mg, yield 3%). $^1$H NMR (CD₃OD 400 MHz): δ 7.62 (s, 1H), 7.33 (s, 1H), 7.24 (dd, J=5.2, 1.2 Hz, 1H), 6.90 (dd, J=5.2, 3.6 Hz, 1H), 6.79 (s, 1H), 6.77 (dd, J=3.6, 0.8 Hz, 1H), 6.66 (dd, J=11.6, 1.6 Hz, 1H), 4.05 (dd, J=8.0, 2.0 Hz, 1H), 3.89 (s, 3H), 3.25 (dd, J=16.4, 8.0 Hz, 1H), 2.64 (dd, J=16.4, 2.0 Hz, 1H). MS (ESI): m/z 413.7 [M+1]$^+$.

Example 18

Synthesis of Intermediates

Intermediate 1: 1-(pyridin-3-yl)-2-(thiophen-3-yl)ethanone

Step 1: Synthesis of nicotinoyl chloride

To a solution of nicotinic acid (2 g, 16.2 mmol) in anhydrous THF (30 mL) was added SOCl₂ (2.4 mL, 32.5 mmol). After stirring at 80° C. for 2 hours, the mixture was concentrated in vacuo

Step 2: Synthesis of ethyl 3-oxo-3-(pyridin-3-yl)-2-(thiophen-3-yl)propanoate To a solution of ethyl 2-(thiophen-3-yl)acetate (2.3 g, 16.2 mmol) in anhydrous THF (20 mL) was added LiHMDS (19.4 mL, 19.44 mmol) at −78° C. After stirring at that temperature for 0.5 h, a solution of nicotinoyl chloride (2.8 g, 16.2 mmol) in anhydrous THF (10 mL) was added into the reaction mixture and stirred at −78° C. for 4 hours. The mixture was quenched with NH₄Cl solution, extracted with EtOAc. The organic layer was concentrated in vacuo and purified by silica gel column chromatography (1.7 g, yield 38%).

Step 3: Synthesis of 1-(pyridin-3-yl)-2-(thiophen-3-yl)ethanone

To a solution of ethyl 3-oxo-3-(pyridin-3-yl)-2-(thiophen-3-yl)propanoate (2 g, 7.26 mmol) in DMSO (20 mL) was added catalytic amount of brine (0.2 mL). The reaction mixture was heated at 160° C. for 2 h. The reaction mixture was cooled to room temperature, diluted with water, and extracted with EtOAc. The organic layer was concentrated in vacuo and purified by column chromatography to afford Intermediate 1 (1 g, yield 68%).

Intermediate 2: Synthesis of 2-phenyl-1-(pyridin-3-yl)ethanone

Step 1

A mixture of nicotinic acid (2 g, 16.2 mmol), N,O-dimethylhydroxylamine hydrochloride (1.6 g, 16.2 mmol), EDCI (3.2 g, 16.2 mmol), HOBT (2.5 g, 16.2 mmol), and Et₃N (6.7 mL, 48.7 mmol) in DCM (30 mL) was stirred at room temperature for 4 h. The mixture was concentrated in vacuo and purified by silica gel column chromatography (PE:EtOAc=2:1) to give product (1.4 g, 52%).

Step 2

To a solution of the above product (Step 1) (500 mg, 3.0 mmol) in anhydrous THF (10 mL) was added benzylmagnesium chloride (2 M/L in THF, 1.8 mL, 3.6 mmol) drop wise at −78° C. The reaction was stirred at −78° C. for 2 h, then quenched with aqueous NH₄Cl and extracted with EtOAc. The organic layer was dried over Na₂SO₄, concentrated in vacuo and purified by column chromatography (PE:EtOAc=5:1) to give Intermediate 2 (110 mg, 19%).

Intermediate 3: 1-(1-methyl-1H-pyrazol-4-yl)-2-(thiophen-3-yl)ethanone

Followed same three step procedure described in Intermediate 1.

Step 1: Synthesis of 1-methyl-1H-pyrazole-4-carbonyl chloride

Started with 1-methyl-1H-pyrazole-4-carboxylic acid, and used toluene instead of THF.

Step 2: Synthesis of ethyl 3-(1-methyl-1H-pyrazol-4-yl)-3-oxo-2-(thiophen-3-yl)propanoate Used crude from step 1 and ethyl 2-(thiophen-3-yl)acetate. After stirring at −78° C., the reaction was warmed to room temperature and stirred overnight.

Step 3: Synthesis of 1-(1-methyl-1H-pyrazol-4-yl)-2-(thiophen-3-yl)ethanone

The reaction mixture was stirred at 180° C. for 2 hours. Purified by silica gel column chromatography (PE:EtOAc=10:1) to give Intermediate 3 (160 mg, yield 61.8%).

Intermediate 4: 1-(1-methyl-1H-pyrazol-4-yl)-2-phenylethanone

Step 1: Synthesis of N-methoxy-N,1-dimethyl-1H-pyrazole-4-carboxamide

A mixture of 1-methyl-1H-pyrazole-4-carboxylic acid (5.0 g, 39.6 mmol), N,O-dimethylhydroxylamine hydrochloride (4.8 g, 48.0 mmol), 1-(3-dimethylaminopropyl)-3-ethylcarbodiimide hydrochloride (9.2 g, 48.0 mmol), hydroxybenzotriazole (6.5 g, 48.0 mmol) and triethylamine (12.1 g, 120 mmol) in dichloromethane (100 mL) was stirred at 9-17° C. overnight. The reaction mixture was diluted with water (50 mL) and the resulting mixture was extracted with EtOAc (30 mL×3), the combined organic layers were washed with brine (50 mL) and dried over anhydrous Na₂SO₄, filtered and concentrated in vacuo (an example of a standard aqueous/EtOAc procedure), then purified by silica gel column chromatography (PE:EtOAc=5:1) to give product (4.6 g, yield 69%).

Step 2: Synthesis of 1-(1-methyl-1H-pyrazol-4-yl)-2-phenylethanone

To a solution of N-methoxy-N,1-dimethyl-1H-pyrazole-4-carboxamide (4.6 g, 27.2 mmol) in anhydrous THF (50 mL) was added benzylmagnesium chloride (2.0 M in THF, 16.7 mL, 32.6 mmol) at −78° C. under N₂, then stirred at the same temperature for 3 hours. The mixture was quenched with saturated NH₄Cl solution, followed by a standard aqueous/EtOAc procedure. The crude was purified by silica gel column chromatography (PE:EtOAc=10:1) to give Intermediate 4 (4.0 g, yield 74%).

Intermediate 5: methyl 4-formyl-2-hydroxybenzoate

Step 1: Synthesis of 4-formyl-2-methoxyphenyl trifluoromethanesulfonate

To a mixture of 4-hydroxy-3-methoxybenzaldehyde (10.0 g, 65.7 mmol) and Et₃N (13.0 g, 128.7 mmol) in anhydrous DCM (100 mL) was added Tf₂O (28.0 g, 99.2 mmol) dropwise at room temperature and the reaction was stirred for 1 hour. The resulting mixture was quenched with water (100 mL) followed by a standard aqueous/EtOAc workup. The residue was purified by silica gel column chromatography (PE:EtOAc=20:1) to give the product as a colorless oil (17.0 g, yield 91%).

Step 2: Synthesis of methyl 4-formyl-2-methoxybenzoate

A mixture of the product from Step 1 (5.0 g, 17.6 mmol), Pd(OAc)₂ (500 mg, 2.2 mmol), dppf (560 mg, 1.0 mmol) and Et₃N (3 mL) in MeOH (30 mL) and DMF (3 mL) was stirred under CO atmosphere (0.5 MPa) at 80° C. overnight. The reaction was cooled to room temperature and filtered. The filtrate was concentrated in vacuo. The residue was purified by column chromatography on silica gel (PE:EtOAc=15:1) to give product as a colorless solid (2.6 g, yield 76%).

Step 3: Synthesis of methyl 4-formyl-2-hydroxybenzoate

A mixture of product from Step 2 (2.6 g, 13.4 mmol) and AlCl₃ (3.6 g, 26.8 mmol) in anhydrous DCM (50 mL) was refluxed for 3 minutes. The resulting mixture was cooled and poured into water (100 mL), followed by a standard aqueous/DCM workup to give Intermediate 5 (2.2 g, yield 92%).

Intermediate 6: Synthesis of 1-phenyl-2-(thiophen-3-yl)ethanone

Step 1: Synthesis of N-methoxy-N-methyl-2-(thiophen-3-yl)acetamide

A mixture of 2-(thiophen-3-yl)acetic acid (2.0 g, 14.1 mmol), O,N-dimethylhydroxylamine (1.68 g, 16.9 mmol), EDCI (2.95 g, 15.5 mmol), HOBT (2.15 g, 15.5 mmol), and TEA (3.7 mL, 31 mmol) in anhydrous DCM (50 mL) was stirred at room temperature under nitrogen for two hours. The reaction mixture was diluted with $CH_2Cl_2$, and the organic layer was washed with aqueous HCl solution (0.5 mol/L, 30 mL×2), saturated $NaHCO_3$ (30 mL×2) and brine(30 mL), dried over $Na_2SO_4$, filtered, and concentrated to give the crude N-methoxy-N-methyl-2-(thiophen-3-yl)acetamide (2.0 g, yield 76.6%).

Step 2: Synthesis of 1-phenyl-2-(thiophen-3-yl)ethanone (Intermediate 2)

To the solution of bromo-benzene (1.0 g, 6.36 mmol) in anhydrous THF (30 mL) was added n-BuLi (5.9 mmol, 2.4 mL) at −78° C. under nitrogen, and the mixture was stirred at −78° C. for further 20 min., a solution of N-methoxy-N-methyl-2-(thiophen-3-yl)acetamide (1 g, 5.4 mmol) in anhydrous THF (10 mL) was added. The resulting mixture was stirred at −78° C. under nitrogen for about 30 min., poured into $NH_4Cl$ aqueous solution, and extracted with EtOAc. The organic layers were washed with brine, dried over sodium sulfate, concentrated, and purified by column chromatography (PE:EtOAc=20:1) to afford Intermediate 6 (600 mg, yield 55.0%).

Intermediate 7: methyl 2-fluoro-4-formyl-6-hydroxybenzoate

Step 1: Synthesis of 2-fluoro-4-formyl-6-methoxyphenyl trifluoromethanesulfonate Followed the procedure described in Intermediate 5, Step 1 where $Tf_2O$ was added at 0° C. and reaction was stirred at 0° C. Yield after purification was 61%.

Step 2: Synthesis of methyl 2-fluoro-4-formyl-6-methoxybenzoate

A mixture of the compound from step 1 (1.1 g, 3.6 mmol), $Pd(OAc)_2$ (200 mg, 0.89 mmol), dppf (200 mg, 0.36 mmol) and $Et_3N$ (2 mL) in MeOH (50 mL) and DMF (2 mL) was stirred under CO atmosphere (50 psi) at 80° C. overnight. The resulting mixture was cooled and filtered. A standard aqueous/EtOAc workup was followed by purification by column chromatography on silica gel (PE:EtOAc=15:1) to give product as an off-white solid (280 mg, yield 36%).

Step 3: Synthesis of methyl 2-fluoro-4-formyl-6-hydroxybenzoate

Followed procedure described in Intermediate 5, step 3 starting with methyl 2-fluoro-4-formyl-6-methoxybenzoate (280 mg, 1.3 mmol) and $AlCl_3$ (350 mg, 2.6 mmol) where reaction was complete after refluxing 10 min. Isolated 250 mg of Intermediate 7, yield 96%.

Intermediate 8: methyl 2-ethoxy-4-formyl-6-hydroxybenzoate

Step 1: Synthesis of ethyl 4-bromo-3,5-diethoxybenzoate

A mixture of 4-bromo-3,5-dihydroxybenzoic acid (2.0 g, 8.6 mmol), EtI (6.7 g, 43.0 mmol) and $K_2CO_3$ (5.9 g, 43.0 mmol) in DMF (20 mL) was stirred at 50° C. overnight. Followed standard aqueous/EtOAc workup (2.5 g, yield 93%).

Step 2: Synthesis of (4-bromo-3,5-diethoxyphenyl)methanol

To a solution of the above from step 1 (5.0 g, 15.8 mmol) in anhydrous THF (50 mL) was added DIBAL-H (1 M in toluene, 80 mL, 80.0 mmol) dropwise at −78° C. under $N_2$ and the reaction was stirred at −78° C. for 2 hours. The resulting mixture was quenched with sat. aq. $NH_4Cl$ (50 mL), followed by a standard aqueous/EtOAc workup to give product (4.2 g, yield 98%).

Step 3: Synthesis of methyl 2,6-diethoxy-4-(hydroxymethyl)benzoate

A mixture of the above from Step 2 (3.0 g, 10.9 mmol), $Pd(OAc)_2$ (500 mg, 2.2 mmol), dppf (500 mg, 0.90 mmol) and $Et_3N$ (5 mL) in MeOH (50 mL) and DMF (10 mL) was stirred under CO atmosphere (5 MPa) at 120° C. for 3 days. The resulting mixture was cooled to room temperature and filtered. The filtrate was diluted with ethyl acetate (200 mL) and washed with brine (50 mL×3). The organic layer was dried over anhydrous $Na_2SO_4$, and concentrated in vacuo. The residue was purified by column chromatography on silica gel (PE:EtOAc=8:1) (1.0 g, yield 36%).

Step 4: Synthesis of methyl 2,6-diethoxy-4-formylbenzoate

A mixture of the above product from Step 3 (1.0 g, 3.9 mmol) and $MnO_2$ (1.0 g, 11.5 mmol) in DCM (30 mL) was refluxed for 1 hour. The mixture was filtered and the filtrate was concentrated in vacuo to give product (950 mg, yield 96%) as an off-white solid.

Step 5: Synthesis of methyl 2-ethoxy-4-formyl-6-hydroxybenzoate

A mixture of methyl 2,6-diethoxy-4-formylbenzoate (950 mg, 3.8 mmol) and $AlCl_3$ (1.0 g, 7.6 mmol) in anhydrous DCM (30 mL) was stirred at 10° C. for 5 minutes. The resulting mixture was poured into water (100 mL) followed by a standard aqueous/EtOAc workup. The residue was purified by column chromatography on silica gel (PE:EtOAc=10:1) to give Intermediate 8 as off-white solid (500 mg, yield 59%).

Intermediate 9: 1-cyclohexyl-2-(thiophen-3-yl)ethanone

Step 1: Synthesis of cyclohexanecarbonyl chloride

Followed the procedure described in Step 1 of Intermediate 1, starting with cyclohexanecarboxylic acid.

Step 2: Synthesis of ethyl 3-cyclohexyl-3-oxo-2-(thiophen-3-yl)propanoate

Followed the procedure described in Step 2 of Intermediate 1. Used crude from step 1 and ethyl 2-(thiophen-3-yl)acetate. Crude product was taken forward without purification.

Step 3: Synthesis of 1-cyclohexyl-2-(thiophen-3-yl)ethanone

Followed the procedure described in Step 3 of Intermediate 1 to give Intermediate 9 (352 mg, 3-step yield 43%).

Intermediate 10: 4-hydroxy-3-(2-hydroxyethoxy)-5-nitrobenzaldehyde

Step 1: Synthesis of 3-(2-hydroxyethoxy)-4-methoxybenzaldehyde

Followed procedure described in Intermediate 8, step 1 starting from 3-hydroxy-4-methoxybenzaldehyde and 2-bromoethanol with the reaction conditions of 90° C. overnight. Isolated 400 mg, yield 62.5%.

Step 2: Synthesis of 4-hydroxy-3-(2-hydroxyethoxyl)benzaldehyde

To the mixture the crude from step 1 (400 mg, 2.0 mmol) in anhydrous DCM (10 mL) was added aluminum chloride (542 mg, 4.0 mmol), and then the mixture was refluxed for 2 days. To the mixture was added dilute HCl and followed by a standard aqueous/EtOH workup. The residue was purified by reverse-phase preparatory HPLC (130 mg, yield 35.2%).

Step 3: Synthesis of 4-hydroxy-3-(2-hydroxyethoxy)-5-nitrobenzaldehyde

To the solution of 4-hydroxy-3-(2-hydroxyethoxyl)benzaldehyde in acetic acid (5 mL) was added 65% nitric acid (34.6 mg, 0.55 mmol) at 0° C., and the mixture was stirred at 0° C. 4 hours. The reaction mixture was poured into ice water followed by a standard aqueous/EtOH workup. Isolated 110 mg, yield 88.7% of Intermediate 10.

Intermediate 11: 2-fluoro-4-formyl-6-hydroxybenzoic acid

A mixture of methyl 2-fluoro-4-formyl-6-hydroxybenzoate (Intermediate 7) (300 mg, 1.50 mmol) and aqueous NaOH (2 M, 10 mL) in MeOH (10 mL) was stirred at 20° C. for 5 hours. The mixture was acidified with aqueous HCl until pH=2 followed by a standard aqueous/EtOH workup. The residue was used for next step without further purification.

Intermediate 12: 1-(1-methyl-1H-pyrazol-4-yl)-2-(thiophen-2-yl)ethanone

Followed same three step procedure described in Intermediate 1.

Step 1: Synthesis of 1-methyl-1H-pyrazole-4-carbonyl chloride

See Intermediate 3, step 1.

Step 2: Synthesis of ethyl 3-(1-methyl-1H-pyrazol-4-yl)-3-oxo-2-(thiophen-2-yl)propanoate Used crude from step 1 and ethyl 2-(thiophen-2-yl)acetate. Crude product was used in next step.

Step 3: Synthesis of 1-(1-methyl-1H-pyrazol-4-yl)-2-(thiophen-3-yl)ethanone

Reaction mixture was stirred at 160° C. for 4 hours. Purified by column chromatography (PE:EtOAc=3:1) to give Intermediate 12 (346 mg, 3-step yield 42%) as brown oil.

Example 19

GSNOR Assays

Various compounds were tested in vitro for their ability to inhibit GSNOR activity. GSNOR inhibitor compounds in Examples 1-17 had an $IC_{50}$ of about <1.0 µM. GSNOR inhibitor compounds in Examples 1-2, 4, 6-7, 9-14, and 17 had an $IC_{50}$ of about less than 0.1 µM. GSNOR expression and purification is described in *Biochemistry* 2000, 39, 10720-10729.

GSNOR Fermentation:

Pre-cultures were grown from stabs of a GSNOR glycerol stock in 2XYT media containing 100 ug/ml ampicillin after an overnight incubation at 37° C. Cells were then added to fresh 2XYT (4 L) containing ampicillin and grown to an OD ($A_{600}$) of 0.6-0.9 at 37° C. before induction. GSNOR expression was induced with 0.1% arabinose in an overnight incubation at 20° C.

GSNOR Purification:

*E. coli* cell paste was lysed by nitrogen cavitation and the clarified lysate purified by Ni affinity chromatography on an AKTA FPLC (Amersham Pharmacia). The column was eluted in 20 mM Tris pH 8.0/250 mM NaCl with a 0-500 mM imidazole gradient. Eluted GSNOR fractions containing the Smt-GSNOR fusion were digested overnight with Ulp-1 at 4° C. to remove the affinity tag then re-run on the Ni column under the same conditions. GSNOR was recovered in the flowthrough fraction and for crystallography is further purified by Q-Sepharose and Heparin flowthrough chromatography in 20 mM Tris pH 8.0, 1 mM DTT, 10 uM $ZnSO_4$.

GSNOR Assay:

GSNO and Enzyme/NADH Solutions are made up fresh each day. The Solutions are filtered and allowed to warm to room temperature. GSNO Solution: 100 mM NaPO4 (pH 7.4), 0.480 mM GSNO. 396 µL of GSNO Solution is added to a cuvette followed by 8 µL of test compound in DMSO (or DMSO only for full reaction control) and mixed with the pipette tip. Compounds to be tested are made up at a stock concentration of 10 mM in 100% DMSO. 2 fold serial dilutions are done in 100% DMSO. 8 µL of each dilution are added to an assay so that the final concentration of DMSO in the assay is 1%. The concentrations of compounds tested range from 100 to 0.003 µM. Enzyme/NADH Solution: 100 mM NaPO4 (pH 7.4), 0.600 mM NADH, 1.0 µg/mL GSNO Reductase. 396 µL of the Enzyme/NADH Solution is added to the cuvette to start the reaction. The cuvette is placed in the Cary 3E UV/Visible Spectrophotometer and the change in 340 nm absorbance/min at 25° C. is recorded for 3 minutes. The assays are done in triplicate for each compound concentration. IC50's for each compound are calculated using the standard curve analysis in the Enzyme Kinetics Module of SigmaPlot.

Final assay conditions: 100 mM NaPO4, pH 7.4, 0.240 mM GSNO, 0.300 mM NADH, 0.5 µg/mL GSNO Reductase and 1% DMSO. Final volume: 800 µL/cuvette.

Example 20

Human NK3 Receptor Binding Assay at 10 µM

Evaluation of the affinity of test compounds for the human neurokinin NK3 receptor from transfected CHO cells was performed using an antagonist radioligand binding assay. Antagonist activity was evaluated at a concentration of 10 µM for a representative subset of test compounds, and the results were expressed as the percent inhibition at that concentration.

Materials and Methods:

Receptor binding assays were performed using crude membranes prepared from CHO cells expressing human NK3 receptor. Osanetant (SR142801), a non-peptide NK3 antagonist, was used as a ligand, and SB222200 was used as a positive control reference compound. The assay was performed with cell membrane homogenates (24 µg protein) incubated for 120 min at 22° C. with 0.4 nM [$^3$H]SR142801 in the absence or presence of the test compound in a buffer containing 20 mM Hepes/NaOH (pH 7.4), 120 mM NaCl, 1 mM $MnCl_2$, 0.01% bacitracin, 0.002% aprotinin and 0.1% BSA. Following incubation, the samples were filtered rapidly under vacuum through glass fiber filters (GF/B, Packard) that had been presoaked with 0.3% PEI. The filters were rinsed several times with ice-cold 50 mM Tris/HCl using a 96-sample cell harvester (Unifilter, Packard), dried, and counted for radioactivity in a scintillation counter (Topcount, Packard) using a scintillation cocktail (Microscint 0, Packard). Each test compound was evaluated at a single concentration of 10 µM. The standard reference compound, SB222200, was tested in each experiment. Nonspecific binding was determined in the presence of 10 µM SB222200. The specific ligand binding to the receptor is defined as the difference between the total binding and the nonspecific binding. The results are expressed as a percent of control specific binding ((measured specific binding/control specific binding)×100) obtained in the presence of the test compounds.

Results: The compounds in the following Examples had about >50% inhibition at 10 µM: Examples 1, 2, and 4.

Example 21

Human NK3 Receptor Binding Assay at 1 uM

Evaluation of the affinity of compounds for the human NK3 receptor from transfected CHO cells was performed using an antagonist radioligand binding assay. Antagonist activity was evaluated at a concentration of 1 µM for a representative subset of test compounds, and the results were expressed as the percent inhibition at that concentration.

Materials and Methods:

Receptor binding assays were performed using crude membranes prepared from CHO cells expressing human NK3 receptor. Osanetant (SR142801), a non-peptide NK3 antagonist, was used as a ligand, and SB222200 was used as a positive control reference compound. The assay was performed with cell membrane homogenates (24 µg protein) incubated for 120 min at 22° C. with 0.4 nM [$^3$H]SR142801 in the absence or presence of the test compound in a buffer containing 20 mM Hepes/NaOH (pH 7.4), 120 mM NaCl, 1 mM $MnCl_2$, 0.01% bacitracin, 0.002% aprotinin and 0.1% BSA. Following incubation, the samples were filtered rapidly under vacuum through glass fiber filters (GF/B, Packard) that had been presoaked with 0.3% PEI. The filters were rinsed several times with ice-cold 50 mM Tris/HCl using a 96-sample cell harvester (Unifilter, Packard), dried, and counted for radioactivity in a scintillation counter (Topcount, Packard) using a scintillation cocktail (Microscint 0, Packard). Each test compound was evaluated at a single concentration of 1 µM. The standard reference compound, SB222200, was tested in each experiment. Nonspecific binding was determined in the presence of 10 µM SB222200. The specific ligand binding to the receptor is defined as the difference between the total binding and the nonspecific binding. The results are expressed as a percent of control specific binding ((measured specific binding/control specific binding)×100) obtained in the presence of the test compounds.

Results: The compounds in the following Examples had about >50% inhibition at 1 µM: Examples 14 and 16.

Example 22

Human NK3 Receptor Binding Assay Determined by $IC_{50}$

Evaluation of the affinity of compounds for the human NK3 receptor from transfected CHO cells was performed using an antagonist radioligand binding assay. The antagonist activity of a representative subset of test compounds was evaluated over a range of concentrations, and the results were expressed as $IC_{50}$ values.

Materials and Methods:

Receptor binding assays were performed using crude membranes prepared from CHO cells expressing human NK3 receptor. Osanetant (SR142801), a non-peptide NK3 antagonist, was used as a ligand, and SB222200 was used as a positive control reference compound. The assay was performed with cell membrane homogenates (24 µg protein) incubated for 120 min at 22° C. with 0.4 nM [$^3$H]SR142801 in the absence or presence of the test compound in a buffer containing 20 mM Hepes/NaOH (pH 7.4), 120 mM NaCl, 1 mM $MnCl_2$, 0.01% bacitracin, 0.002% aprotinin and 0.1% BSA. Following incubation, the samples were filtered rapidly under vacuum through glass fiber filters (GF/B, Packard) that had been presoaked with 0.3% PEI. The filters were rinsed several times with ice-cold 50 mM Tris/HCl using a 96-sample cell harvester (Unifilter, Packard), dried, and counted for radioactivity in a scintillation counter (Topcount, Packard) using a scintillation cocktail (Microscint 0, Packard). For $IC_{50}$ generation, test compounds were assayed at 8 concentrations within the range of $1\times10^{-5}$ to $1\times10^{-10}$ M (10 µM to 100 µM). The standard reference compound, SB222200, was tested in each experiment. Nonspecific binding was determined in the presence of 10 µM SB222200. The specific ligand binding to the receptor is defined as the difference between the total binding and the nonspecific binding. The $IC_{50}$ values (concentration causing a half-maximal inhibition of control specific binding) and Hill coefficients (nH) were determined by non-linear regression analysis of the competition curves generated with mean replicate values using Hill equation curve fitting ($Y=D+[(A-D)/(1+(C/C_{50})^{nH})]$, where Y=specific binding, D=minimum specific binding, A=maximum specific binding, C=compound concentration, $C_{50}=IC_{50}$, and nH=slope factor). This analysis was performed using software developed at Cerep (Hill software) and validated by comparison with data generated by the commercial software SigmaPlot® 4.0 for Windows® (©

1997 by SPSS Inc.). The inhibition constants ($K_i$) were calculated using the Cheng Prusoff equation ($K_i=IC_{50}/(1+(L/K_D))$, where L=concentration of radioligand in the assay, and $K_D$=affinity of the radioligand for the receptor). A scatchard plot was used to determine the Kd.

Results: Compound 1 in Example 1 had an $IC_{50}$ of about 1.1 µM.

Example 23

Efficacy of GSNORi in Experimental Asthma

Experimental Asthma Model:
A mouse model of ovalbumin (OVA)-induced asthma is used to screen GSNOR inhibitors for efficacy against methacholine (MCh)-induced bronchoconstriction/airway hyperreactivity. This is a widely used and well characterized model that presents with an acute, allergic asthma phenotype with similarities to human asthma. Efficacy of GSNOR inhibitors are assessed using a prophylactic protocol in which GSNOR inhibitors are administered prior to challenge with MCh. Bronchoconstriction in response to challenge with increasing doses of MCh is assessed using whole body plethysmography ($P_{enh}$; Buxco). The amount of eosinophil infiltrate into the bronchoaveolar lavage fluid (BALF) is also determined as a measure of lung inflammation. The effect of GSNOR inhibitors are compared to vehicles and to Combivent (inhaled; IH) as the positive control
  Materials and Methods
  Allergen Sensitization and Challenge Protocol
OVA (500 µg/ml) in PBS is mixed with equal volumes of 10% (w/v) aluminum potassium sulfate in distilled water and incubated for 60 min. at room temperature after adjustment to pH 6.5 using 10 N NaOH. After centrifugation at 750×g for 5 min, the OVA/alum pellet is resuspended to the original volume in distilled water. Mice receive an intraperitoneal (IP) injection of 100 µg OVA (0.2 mL of 500 µg/mL in normal saline) complexed with alum on day 0. Mice are anesthetized by IP injection of a 0.2-mL mixture of ketamine and xylazine (0.44 and 6.3 mg/mL, respectively) in normal saline and are placed on a board in the supine position. Two hundred fifty micrograms (100 µl of a 2.5 mg/ml) of OVA (on day 8) and 125 µg (50 µl of 2.5 mg/ml) OVA (on days 15, 18, and 21) are placed on the back of the tongue of each animal.
  Pulmonary Function Testing (Penh)
In vivo airway responsiveness to methacholine is measured 24 h after the last OVA challenge in conscious, freely moving, spontaneously breathing mice with whole body plethysmography using a Buxco chamber (Wilmington, N.C.). Mice are challenged with aerosolized saline or increasing doses of methacholine (5, 20 and 50 mg/mL) generated by an ultrasonic nebulizer for 2 min. The degree of bronchoconstriction is expressed as enhanced pause ($P_{enh}$), a calculated dimensionless value, which correlates with the measurement of airway resistance, impedance, and intrapleural pressure in the same mouse. $P_{enh}$ readings are taken and averaged for 4 min. after each nebulization challenge. $P_{enh}$ is calculated as follows: $P_{enh}=[(T_e/T_r-1)\times(PEF/PIF)]$, where $T_e$ is expiration time, $T_r$ is relaxation time, PEF is peak expiratory flow, and PIF is peak inspiratory flow×0.67 coefficient. The time for the box pressure to change from a maximum to a user-defined percentage of the maximum represents the relaxation time. The $T_r$ measurement begins at the maximum box pressure and ends at 40%.
  Eosinophil Infiltrate in BALF
After measurement of airway hyper-reactivity, the mice are exsanguinated by cardiac puncture, and then BALF is collected from either both lungs or from the right lung after tying off the left lung at the mainstem bronchus. Total BALF cells are counted from a 0.05 mL aliquot, and the remaining fluid is centrifuged at 200×g for 10 min at 4° C. Cell pellets are resuspended in saline containing 10% BSA with smears made on glass slides. Eosinophils are stained for 5 min. with 0.05% aqueous eosin and 5% acetone in distilled water, rinsed with distilled water, and counterstained with 0.07% methylene blue.
  GSNOR Inhibitors and Controls
GSNOR inhibitors are reconstituted in phosphate buffered saline (PBS), pH 7.4, at concentrations ranging from 0.00005 to 3 mg/mL. GSNOR inhibitors are administered to mice (10 mL/kg) as a single dose either intravenously (IV) or orally via gavage. Dosing is performed from 30 min. to 24 h prior to MCh challenge. Effect of GSNOR inhibitors are compared to PBS vehicle dosed in the same manner.

Combivent is used as the positive control in all studies. Combivent (Boehringer Ingelheim) is administered to the lung using the inhaler device supplied with the product, but adapted for administration to mice, using a pipet tip. Combivent is administered 48 h, 24 h, and 1 h prior to MCh challenge. Each puff (or dose) of Combivent provides a dose of 18 µg ipatropium bromide (IpBr) and 103 µg albuterol sulfate or approximately 0.9 mg/kg IpBr and 5 mg/kg albuterol.
  Statistical Analyses
Area under the curve values for $P_{enh}$ across baseline, saline, and increasing doses of MCh challenge are calculated using GraphPad Prism 5.0 (San Diego, Calif.) and expressed as a percent of the respective (IV or orally administered) vehicle control. Statistical differences among treatment groups and the respective vehicle control group within each study are calculated using one-way ANOVA, Dunnetts (JMP 8.0, SAS Institute, Cary, N.C.). A p value of <0.05 among the treatment groups and the respective vehicle control group is considered significantly different.

Example 24

Mouse Pharmacokinetic (PK) Study

Experimental Model
The mouse is used to determine the pharmacokinetics of compounds of the invention. This species is widely used to assess the bioavailability of compounds by administering both oral (PO) and intravenous (IV) test articles. Efficacy of the compounds of the invention are compared by assessing plasma exposure in male BALB/c mice either via IV or PO administration at the times of peak activity.
  Materials and Methods
  IV Administration of Compounds of the Invention
Compounds of the invention are reconstituted in a phosphate buffered saline (PBS)/10% Solutol (HS 15) clear solution resulting in a concentration of 0.2 mg/mL and administered to mice (2 mg/kg) as a single IV dose. Animals dosed via the lateral tail vein. Blood samples are collected at designated time points (0.083, 0.25, 0.5, 1, 2, 4, 8, 16, 24 hours) by cardiac puncture under isoflurane anesthesia (up to 1 mL blood per animal). The blood is collected into tubes containing Li-Heparin. The blood samples are kept on ice until centrifugation within approximately 30 minutes of collection. The plasma is transferred into labeled polypropylene tubes and frozen at −70° C. until analyzed by LC/MS/MS.
  PO Administration of Compounds of the Invention
The compounds of the invention are reconstituted in 40% Propylene Glycol/40% Propylene Carbonate/20% of a 5%

Sucrose clear solution resulting in a concentration of 2 mg/mL and administered to mice (10 mg/kg) as a single oral dose via gavage. Blood samples are collected at 0.25, 0.5, 1, 2, 4, 8, 12, 16, 20 and 24 hours post dose by cardiac puncture under isoflurane anesthesia. The blood is collected in tubes containing Li-Heparin. The blood samples are kept on ice until centrifugation within approximately 30 minutes of collection. The plasma is transferred into labeled polypropylene tubes and frozen at −70° C. until analyzed by LC/MS/MS.

LC/MS/MS Analysis

Plasma samples at each timepoint were analyzed using a LC-MS/MS with a lower limit of quantification (LLOQ) of 1 ng/mL. Plasma was analyzed to determine the amount of the compound of the invention in each sample and regression curves generated for each compounds of the invention in the relevant matrixes.

WinNonlin analysis was used for calculating PK parameters for both the IV and PO administrations:

PK parameters for IV portion—$AUC_{last}$; $AUC_{INF}$; T1/2; Cl; Vss; $C_{max}$; MRT PK parameters for PO portion—$AUC_{last}$; $AUC_1$; T1/2; $C_{max}$; Cl, MRT.

In addition to the above PK parameters, bioavailability (% F) was calculated.

Results: Compound 6 had an oral bioavailability of 22%.

Example 25

Efficacy of GSNOR Inhibitors in Experimental Inflammatory Bowel Disease (IBD)

Experimental Model

An acute model of dextran sodium sulfate (DSS)-induced IBD in mice is used to explore efficacy of GSNOR inhibitors against this disease. Acute DSS-induced IBD is a widely used and well characterized model that induces pathological changes in the colon similar to those observed in the human disease. In this model and in human disease, epithelial cells within the crypts of the colon are disrupted, leading to dysfunction of the epithelial barrier and the ensuing tissue inflammation, edema, and ulceration. GSNOR inhibitor therapy may benefit IBD by restoring s-nitrosogluthathione (GSNO) levels, and thus prevent or reverse the epithelial barrier dysfunction.

Experimental IBD is induced by administration of DSS in the drinking water over several days. GSNOR inhibitors are administered daily via intravenous (IV) dosing. Effect of treatment is assessed via endoscopy and histopathology using a five point scale ranging from a score=0 (normal tissue) to a score=4 (ulcerative tissue damage and marked pathological changes). The effect of GSNOR inhibitors is compared to vehicle treated controls. The corticosteroid, prednisolone, is used as the positive control in this study and is administered daily via oral dosing. Naïve mice are also assessed as a normal tissue control.

Materials and Methods

Experimental IBD is induced by administration of 3% DSS in the drinking water on study days 0 to 5. GSNOR inhibitors are reconstituted to concentrations of 0.2 and 2 mg/ml in phosphate buffered saline (PBS), pH 7.4. Mice are treated daily via IV administration of 0.1 ml GSNOR inhibitor solution per mouse for doses of 1 and 10 mg/kg/day. GSNOR inhibitor dosing is started 2 days prior to the DSS administration and continued through the last day of the study (days −2 to 7). PBS is used as the vehicle control and is administered in the same manner as the GSNOR inhibitor. The corticosteroid, prednisolone, is used as the positive control for the study, and is administered orally at a dose of 3 mg/kg/day on each day (study days −2 to 7).

The effect of drug treatment is assessed on day 7 via endoscopy and histopathology. Mice are first anesthetized with inhaled isoflurane and subjected to endoscopy using a veterinary endoscope (Karl Storz Veterinary Endoscopy America, Inc., Goleta, Calif.). Each mouse is scored for mucosal injury using the endoscopy scoring criteria. An endoscopy score of 0 is normal, 1 is loss of vascularity, 2 is loss of vascularity and friability, 3 is friability and erosions, and 4 is ulcerations and bleeding. Following endoscopy, mice are euthanized via asphyxiation with inhaled carbon dioxide. Colon sections are then formalin-fixed, paraffin-embedded, sectioned, and stained with hematoxylin-eosin. Colon sections are examined via light microscopy and scored in a blinded fashion by a board certified veterinary pathologist with particular expertise in GI pathology. Pathological changes to the epithelium, connective tissue, and submucosa are scored based on inflammation, edema, and necrosis, and a score of 0 is normal, 1 is minimal, 2 is mild, 3 is moderate, and 4 is marked.

Example 26

Efficacy of GSNOR Inhibitors in Experimental Chronic Obstructive Pulmonary Disease (COPD)

Experimental COPD Model

An acute model of elastase-induced COPD in mice is used to explore efficacy of GSNOR inhibitors against this disease. Elastase-induced COPD is a widely used and well characterized model that induces pathological changes in the lung similar to those observed in the human disease. In this model and in human disease, airway obstruction, pulmonary inflammation, and airspace enlargement are evident. GSNOR inhibitor therapy may benefit COPD through the bronchodilatory and anti-inflammatory actions of these compounds.

Experimental COPD is induced by administration of the elastases, papain and porcine pancreatic elastase (PPE), into the lung over several days. GSNOR inhibitors are administered daily via oral dosing. Efficacy is determined by assessing the ability of GSNOR inhibitors to attenuate bronchoconstriction in response to methacholine (MCh) aerosol challenge, decrease pulmonary inflammation, and reduce airspace enlargement in the aveoli. The effect of GSNOR inhibitors are compared to vehicle treated controls. A combination of daily oral SP CXC receptor 2/receptor 1 (SP CXCR2/1) antagonist, which blocks recruitment of neutrophils and monocytes, and inhaled Flovent (fluticasone; corticosteroid), is used as the positive control in this study.

Materials and Methods

Experimental COPD is induced by administration of 80 µg papain and 20 U/mg PPE per mouse per day via intra-tracheal (IT) instillation on study days 0 to 7. GSNOR inhibitor is reconstituted to concentrations of 0.01, 0.1, and 1 mg/ml in phosphate buffered saline (PBS), pH 7.4. Mice are treated daily via oral administration (gavage) of 0.1 ml GSNORi solution per mouse for doses of 0.1, 1, and 10 mg/kg/day. PBS is used as the vehicle control and is administered via daily oral dosing. The small molecule antagonist SP CXCR2/R1 (Schering-Plough/Merck), which blocks receptors to cytokine chemoattractants for neutrophil and monocyte recruitment, is used in combination with the corticosteroid, Flovent (Glaxo), as the positive control for the study. SP CXCR2/R1 is dosed orally at 50 mg/kg/day. Flovent is dosed via inhalation at 220 µg/mouse/day. One group of mice is treated with GSNOR inhibitor, vehicle control, or positive control for 7 days (study days 8 to 14), while a second group of mice is treated with GSNOR inhibitor, vehicle control, or positive control for 14 days (study days 8 to 21).

The effect of drug treatment is assessed 7 and 14 days post-treatment by measuring attenuation of methacholine-induced bronchoconstriction (bronchodilatory effect), attenuation of pulmonary inflammation, and reduction of airspace enlargement in the alveoli (14 day post-treatment only).

Bronchodilatory Effect

In vivo airway responsiveness to methacholine is measured in conscious, freely moving, spontaneously breathing mice with whole body plethysmography using a Buxco chamber (Wilmington, N.C.). Mice are challenged with aerosolized saline or increasing doses of methacholine (5, 20, and 50 mg/ml) generated by an ultrasonic nebulizer for 2 min. The degree of bronchoconstriction is expressed as enhanced pause (Penh), a calculated dimensionless value, which correlated with the measurement of airway resistance, impedance, and intrapleural pressure in the same mouse. Penh readings are taken and averaged for 4 min. after each nebulization challenge. Penh is calculated as follows: $Penh=[(T_e/T_r-1)\times(PEF/PIF)]$, where $T_e$ is expiration time, $T_r$ is relaxation time, PEF is peak expiratory flow, and PIF is peak inspiratory flow$\times 0.67$ coefficient. The time for the box pressure to change from a maximum to a user-defined percentage of the maximum represented the relaxation time. The $T_r$ measurement began at the maximum box pressure and ended at 40%.

Anti-Inflammatory Effect

After measurement of airway hyper-reactivity, the mice are exsanguination by cardiac puncture, and then bronchoalveolar lavage fluid (BALF) is collected from the right lung after tying off the left lung at the mainstem bronchus. Total BALF cells are counted, and the remaining fluid is centrifuged at 200×g for 10 min. at 4° C. Cell pellets are resuspended in saline containing 10% bovine serum albumin (BSA) and smears are made on glass slides using cytospin. Cells are stained with Diff-Quik for white blood cell (WBC) differential counts via light microscopy. Epithelial cells are counted and subtracted from the total number of cells. The proportions of eosinophils, macrophages, neutrophils, and lymphocytes are counted using standard morphological criteria and expressed as a percentage of the total number of white blood cells (WBCs).

The ability of treatment to reduce levels of neutrophil and monocyte chemoattractants in the BALF are also assessed as additional parameters of anti-inflammatory effect. KC (keratinocyte chemoattractant), also known as GROα (growth-related oncogene alpha), and JE (MCP-1, monocyte chemoattractant protein), chemokines for neutrophil and monocyte recruitment, respectively, are measured using immunoassay.

Reduction of Airspace Enlargement

Both lungs are inflated under constant positive pressure at 25 cm water pressure with 10% buffered formaldehyde and then perfused-fixed. The fixed lungs are embedded in paraffin, stained with hematoxylin and eosin, and examined via light microscopy. Airspace enlargement is quantified morphologically by calculating the mean linear intercept (Lm) and average equivalent diameter of alveoli (D2).

It will be apparent to those skilled in the art that various modifications and variations can be made in the methods and compositions of the present invention without departing from the spirit or scope of the invention.

What is claimed is:

1. A method of treatment of a disease or condition wherein the disease or condition is selected from the group consisting of pulmonary disorders, inflammatory bowel disease, schizophrenia, psychosis, anxiety, and depression, which comprises administering a therapeutically effective amount of a compound of formula I or a pharmaceutically acceptable salt thereof to a patient in need thereof

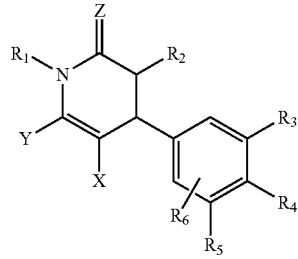

Formula I wherein

X is selected from the group consisting of phenyl, substituted phenyl, thiophen-yl, substituted thiophen-yl, thiazol-yl, substituted thiazol-yl, pyrazin-yl, substituted pyrazin-yl, pyridin-yl, and substituted pyridin-yl, cyclohexyl, substituted cyclohexyl;

Y is selected from the group consisting of phenyl, substituted phenyl, thiophen-yl, substituted thiophen-yl, thiazol-yl, substituted thiazol-yl, pyrazin-yl, substituted pyrazin-yl, pyridin-yl, substituted pyridin-yl, furan-yl, substituted furan-yl, benzo[d][1,3]dioxol-yl, substituted benzo[d][1,3]dioxol-yl, imidazol-yl, substituted imidazol-yl, naphthalen-yl, substituted naphthalen-yl, pyrrol-yl, substituted pyrrol-yl, pyrazol-yl, substituted pyrazol-yl, tetrahydrofuran-yl, substituted tetrahydrofuran-yl, cyclopentyl, substituted cyclopentyl, cyclohexyl, and substituted cyclohexyl;

Z is selected from the group consisting of 0, S, and NRS;

$R_1$ and $R_2$ and $R_7$ are independently selected from the group consisting of hydrogen, and $C_1$-$C_6$ alkyl;

$R_3$ is selected from the group consisting of hydrogen, nitro, cyano, carboxyl, carbamoyl, methylsulfonamido, fluoro, chloro, bromo, hydroxy, methylsulfonyl, and methylsulfinyl, isoxazol-4-yl, $C_1$-$C_6$ alkoxy, —C(NH)NHOH, sulfonic acid, and acetyl;

$R_4$ is selected from the group consisting of hydroxyl, carboxyl, and tetrazol-5-yl;

$R_5$ is selected from the group consisting of hydrogen, hydroxyl, carboxy, chloro, fluoro, cyano, —O(CH$_2$)$_{1-6}$NMe$_2$, $C_1$-$C_6$ alkyl, —O(CH$_2$)$_{1-6}$OCH$_3$, —O(CH$_2$)$_{1-6}$OH, acetyl, CF$_3$, and $C_1$-$C_6$ alkoxy; and $R_6$ is selected from the group consisting of hydrogen and hydroxyl.

2. The method of claim 1 wherein $R_1$, $R_2$ and $R_7$ are independently selected from the group consisting of hydrogen and methyl;

$R_5$ is selected from the group consisting of hydrogen, hydroxyl, carboxyl, chloro, fluoro, cyano, —O(CH$_2$)$_2$NMe$_2$, $C_1$-$C_6$ alkyl, —O(CH$_2$)$_2$OCH$_3$, —O(CH$_2$)$_2$OH, acetyl, CF$_3$, methoxy, ethoxy, isopropoxy, and n-propoxy; and $R_6$ is hydrogen.

3. The method of claim 1 wherein $R_3$ is selected from the group consisting of hydrogen, nitro, and hydroxyl; and $R_5$ is selected from the group consisting of hydrogen, ethoxy, fluoro, and —O(CH$_2$)$_2$OH.

4. The method of claim 1 wherein X is selected from the group consisting of phenyl, thiophen-2-yl, thiophen-3-yl, thiazol-2-yl, 2-fluorophenyl, p-tolyl, m-tolyl, biphenyl-4-yl, 4-methoxyphenyl, 3-chlorophenyl, 3,4-dichlorophenyl, 3-methoxyphenyl, 3,4-dimethoxyphenyl, 4-bromophenyl, o-tolyl, 4-chlorophenyl, 2-chlorophenyl, 3-cyanophenyl, 3,4-difluorophenyl, 4-cyanophenyl, 3-carbamoylphenyl, pyrazin-2-yl, biphenyl-3-yl, 2-cyanophenyl, pyridin-4-yl, and pyridin-3-yl, 4-(dimethylamino)phenyl, 3-fluorophenyl, 3-ethylphenyl, and cyclohexyl.

5. The method of claim 1 wherein X is selected from the group consisting of phenyl, thiophen-2-yl, thiophen-3-yl, and pyridin-3-yl.

6. The method of claim 1 wherein Y is selected from the group consisting of phenyl, 3-methoxyphenyl, p-tolyl, 4-methoxyphenyl, 3,5-dichlorophenyl, 3-fluorophenyl, 4-bromophenyl, biphenyl-4-yl, 4-fluorophenyl, 4-chlorophenyl, 3-chlorophenyl, 3,4-dimethoxyphenyl, 3-fluoro-4-methoxyphenyl, 4-chloro-3-fluorophenyl, 3-chloro-4-fluorophenyl, 3,4-difluorophenyl, 3,5-difluorophenyl, 3,4-dichlorophenyl, 4-hydroxyphenyl, 2,4-difluorophenyl, furan-3-yl, 2-chlorophenyl, 3-cyanophenyl, 4-(dimethylamino)phenyl, 2-fluorophenyl, 4-morpholinophenyl, 4-aminophenyl, pyridin-2-yl, benzo[d][1,3]dioxol-5-yl, 4-cyanophenyl, pyridin-3-yl, pyridin-4-yl, 4-acetamidophenyl, thiophen-2-yl, thiophen-3-yl, 1-methyl-1H-imidazol-4-yl, naphthalen-1-yl, methyl phenylcarbamate, and naphthalen-2-yl, 4-(methanesulfonamido)phenyl, 1H-pyrrol-3-yl, 1-(phenylsulfonyl)-1H-pyrrol-3-yl, furan-2-yl, 4-(trifluoromethyl)phenyl, o-tolyl, 1-methyl-1H-pyrazol-4-yl, 1-methyl-1H-pyrazol-3-yl, 3-chloro-5-fluorophenyl, 3-hydroxyphenyl, pyrazin-2-yl, quinolin-6-yl, isoquinolin-6-yl, 1-methyl-1H-pyrazol-5-yl, tetrahydrofuran-2-yl, cyclopentyl, tetrahydrofuran-3-yl and cyclohexyl.

7. The method of claim 1 wherein Y is selected from the group consisting of phenyl, pyridin-3-yl, 1-methyl-1H-pyrazol-4-yl, and cyclohexyl.

8. The method of claim 1 wherein Z is O.

9. The method of claim 1 wherein the compound is selected from the group consisting of
   4-(3-ethoxy-4-hydroxy-5-nitrophenyl)-5,6-diphenyl-3,4-dihydropyridin-2(1H)-one;
   4-(3-ethoxy-4-hydroxy-5-nitrophenyl)-6-(pyridin-3-yl)-5-(thiophen-3-yl)-3,4-dihydropyridin-2(1H)-one;
   4-(4-(2H-tetrazol-5-yl)phenyl)-5-phenyl-6-(pyridin-3-yl)-3,4-dihydropyridin-2(1H)-one;
   4-(3-ethoxy-4-hydroxy-5-nitrophenyl)-6-(1-methyl-1H-pyrazol-4-yl)-5-(thiophen-3-yl)-3,4-dihydropyridin-2(1H)-one;
   4-(4-(2H-tetrazol-5-yl)phenyl)-6-(1-methyl-1H-pyrazol-4-yl)-5-(thiophen-3-yl)-3,4-dihydropyridin-2(1H)-one;
   2-hydroxy-4-(2-oxo-5,6-diphenyl-1,2,3,4-tetrahydropyridin-4-yl)benzoic acid;
   2-hydroxy-4-(2-oxo-6-phenyl-5-(thiophen-3-yl)-1,2,3,4-tetrahydropyridin-4-yl)benzoic acid;
   4-(4-(2H-tetrazol-5-yl)phenyl)-6-(1-methyl-1H-pyrazol-4-yl)-5-phenyl-3,4-dihydropyridin-2(1H)-one;
   2-hydroxy-4-(6-(1-methyl-1H-pyrazol-4-yl)-2-oxo-5-(thiophen-3-yl)-1,2,3,4-tetrahydropyridin-4-yl)benzoic acid;
   2-fluoro-6-hydroxy-4-(2-oxo-5,6-diphenyl-1,2,3,4-tetrahydropyridin-4-yl)benzoic acid;
   2-fluoro-6-hydroxy-4-(6-(1-methyl-1H-pyrazol-4-yl)-2-oxo-5-(thiophen-3-yl)-1,2,3,4-tetrahydropyridin-4-yl) benzoic acid;
   2-ethoxy-6-hydroxy-4-(2-oxo-5,6-diphenyl-1,2,3,4-tetrahydropyridin-4-yl)benzoic acid;
   4-(6-cyclohexyl-2-oxo-5-(thiophen-3-yl)-1,2,3,4-tetrahydropyridin-4-yl)-2-fluoro-6-hydroxybenzoic acid;
   4-(4-hydroxy-3-(2-hydroxyethoxy)-5-nitrophenyl)-5,6-diphenyl-3,4-dihydropyridin-2(1H)-one;
   2-fluoro-6-hydroxy-4-(1-methyl-2-oxo-5,6-diphenyl-1,2,3,4-tetrahydropyridin-4-yl)benzoic acid;
   4-(3-ethoxy-4-hydroxy-5-nitrophenyl)-1-methyl-5,6-diphenyl-3,4-dihydropyridin-2(1H)-one; and
   2-fluoro-6-hydroxy-4-(6-(1-methyl-1H-pyrazol-4-yl)-2-oxo-5-(thiophen-2-yl)-1,2,3,4-tetrahydropyridin-4-yl) benzoic acid.

10. The method of claim 1 wherein the disease or condition is a pulmonary disorder.

11. The method of claim 10 wherein the pulmonary disorder is selected from the group consisting of asthma, cystic fibrosis, and chronic obstructive pulmonary disorder (COPD).

12. The method of claim 1 wherein the disease or condition is inflammatory bowel disease (IBD).

13. The method of claim 1 wherein the disease or condition is selected from the group consisting of anxiety, depression, psychosis and schizophrenia.

14. A method of inhibiting S-nitrosoglutathione reductase (GSNOR) in a subject, said method comprising administering to the subject a pharmacologically effective amount of a pharmaceutical composition comprising the compound of formula I as defined in claim 1 or a pharmaceutically acceptable salt thereof.

15. The method of claim 14 wherein the compound of formula I is the S enantiomer.

16. The method of claim 14 wherein the compound is selected from the group consisting of
   4-(3-ethoxy-4-hydroxy-5-nitrophenyl)-5,6-diphenyl-3,4-dihydropyridin-2(1H)-one;
   4-(3-ethoxy-4-hydroxy-5-nitrophenyl)-6-(pyridin-3-yl)-5-(thiophen-3-yl)-3,4-dihydropyridin-2(1H)-one;
   4-(4-(2H-tetrazol-5-yl)phenyl)-5-phenyl-6-(pyridin-3-yl)-3,4-dihydropyridin-2(1H)-one;
   4-(3-ethoxy-4-hydroxy-5-nitrophenyl)-6-(1-methyl-1H-pyrazol-4-yl)-5-(thiophen-3-yl)-3,4-dihydropyridin-2(1H)-one;
   4-(4-(2H-tetrazol-5-yl)phenyl)-6-(1-methyl-1H-pyrazol-4-yl)-5-(thiophen-3-yl)-3,4-dihydropyridin-2(1H)-one;
   2-hydroxy-4-(2-oxo-5,6-diphenyl-1,2,3,4-tetrahydropyridin-4-yl)benzoic acid;
   2-hydroxy-4-(2-oxo-6-phenyl-5-(thiophen-3-yl)-1,2,3,4-tetrahydropyridin-4-yl)benzoic acid;
   4-(4-(2H-tetrazol-5-yl)phenyl)-6-(1-methyl-1H-pyrazol-4-yl)-5-phenyl-3,4-dihydropyridin-2(1H)-one;
   2-hydroxy-4-(6-(1-methyl-1H-pyrazol-4-yl)-2-oxo-5-(thiophen-3-yl)-1,2,3,4-tetrahydropyridin-4-yl)benzoic acid;
   2-fluoro-6-hydroxy-4-(2-oxo-5,6-diphenyl-1,2,3,4-tetrahydropyridin-4-yl)benzoic acid;
   2-fluoro-6-hydroxy-4-(6-(1-methyl-1H-pyrazol-4-yl)-2-oxo-5-(thiophen-3-yl)-1,2,3,4-tetrahydropyridin-4-yl) benzoic acid;
   2-ethoxy-6-hydroxy-4-(2-oxo-5,6-diphenyl-1,2,3,4-tetrahydropyridin-4-yl)benzoic acid;
   4-(6-cyclohexyl-2-oxo-5-(thiophen-3-yl)-1,2,3,4-tetrahydropyridin-4-yl)-2-fluoro-6-hydroxybenzoic acid;
   4-(4-hydroxy-3-(2-hydroxyethoxy)-5-nitrophenyl)-5,6-diphenyl-3,4-dihydropyridin-2(1H)-one;
   2-fluoro-6-hydroxy-4-(1-methyl-2-oxo-5,6-diphenyl-1,2,3,4-tetrahydropyridin-4-yl)benzoic acid;
   4-(3-ethoxy-4-hydroxy-5-nitrophenyl)-1-methyl-5,6-diphenyl-3,4-dihydropyridin-2(1H)-one; and
   2-fluoro-6-hydroxy-4-(6-(1-methyl-1H-pyrazol-4-yl)-2-oxo-5-(thiophen-2-yl)-1,2,3,4-tetrahydropyridin-4-yl) benzoic acid.

17. A method of antagonizing the tachkinin receptor NK3 in a subject, said method comprising administering to the subject a pharmacologically effective amount of a pharmaceutical composition comprising the compound of formula I as defined in claim 1 or a pharmaceutically acceptable salt thereof.

18. The method of claim 17 wherein the compound of formula I is the R enantiomer.

19. The method of claim 17 wherein the compound is selected from the group consisting of
- 4-(3-ethoxy-4-hydroxy-5-nitrophenyl)-5,6-diphenyl-3,4-dihydropyridin-2(1H)-one;
- 4-(3-ethoxy-4-hydroxy-5-nitrophenyl)-6-(pyridin-3-yl)-5-(thiophen-3-yl)-3,4-dihydropyridin-2(1H)-one
- 4-(3-ethoxy-4-hydroxy-5-nitrophenyl)-6-(1-methyl-1H-pyrazol-4-yl)-5-(thiophen-3-yl)-3,4-dihydropyridin-2(1H)-one;
- 4-(4-hydroxy-3-(2-hydroxyethoxy)-5-nitrophenyl)-5,6-diphenyl-3,4-dihydropyridin-2(1H)-one; and
- 4-(3-ethoxy-4-hydroxy-5-nitrophenyl)-1-methyl-5,6-diphenyl-3,4-dihydropyridin-2(1H)-one.

\* \* \* \* \*